(12) United States Patent
Scott et al.

(10) Patent No.: US 11,672,559 B2
(45) Date of Patent: Jun. 13, 2023

(54) SURGICAL STAPLER WITH CARTRIDGE PAN RETENTION FEATURES

(71) Applicant: Cilag GmbH International, Zug (CH)

(72) Inventors: Gregory G. Scott, Cincinnati, OH (US); Ryan W. McGhee, Cincinnati, OH (US); Patrick M. Schleitweiler, West Chester, OH (US); Stephen J. Balek, Springboro, OH (US); Thomas W. Lytle, IV, Liberty Township, OH (US); Bryan R. Keller, Loveland, OH (US); Mollie Casey, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 130 days.

(21) Appl. No.: 16/903,678

(22) Filed: Jun. 17, 2020

(65) Prior Publication Data

US 2021/0393287 A1    Dec. 23, 2021

(51) Int. Cl.
*A61B 17/072* (2006.01)
*A61B 17/32* (2006.01)
*A61B 17/00* (2006.01)

(52) U.S. Cl.
CPC .... *A61B 17/320092* (2013.01); *A61B 17/072* (2013.01); *A61B 2017/00398* (2013.01);
(Continued)

(58) Field of Classification Search
CPC .......... A61B 17/320092; A61B 17/072; A61B 2017/320095; A61B 2017/0725; A61B 2017/07264; A61B 2017/07271; A61B 2017/07278; A61B 2017/07285; A61B 2017/320097; A61B 2017/00398; A61B 2017/00526; A61B 2017/07214;
(Continued)

(56) References Cited

U.S. PATENT DOCUMENTS

| 4,805,823 A | 2/1989 | Rothfuss |
| 5,415,334 A | 5/1995 | Williamson, IV et al. |

(Continued)

FOREIGN PATENT DOCUMENTS

| EP | 3338703 A1 * | 6/2018 | ........... A61B 17/064 |
| EP | 3547325 A1 * | 10/2019 | ......... A61B 17/0682 |

OTHER PUBLICATIONS

International Search Report and Written Opinion dated Oct. 6, 2021 for Application No. PCT/EP2021/066298, 11 pgs.

*Primary Examiner* — Stephen F. Gerrity
*Assistant Examiner* — Linda J Hodge
(74) *Attorney, Agent, or Firm* — Frost Brown Todd LLP

(57) ABSTRACT

A surgical instrument end effector includes a first jaw, a second jaw, a staple cartridge, and a retention cap. The second jaw including an anvil having a plurality of staple forming pockets. The first and second jaws are operable to clamp and staple tissue positioned therebetween. The staple cartridge is configured for receipt within the first jaw. The staple cartridge includes a cartridge body, a lower tray, and a plurality of staples. The cartridge body and the lower tray are configured to couple together. The retention cap is configured to fasten to a proximal end of the cartridge body and to engage the lower tray. The retention cap is further configured to fix the position of the lower tray relative to the cartridge body.

20 Claims, 20 Drawing Sheets

(52) U.S. Cl.
CPC ............... *A61B 2017/00526* (2013.01); *A61B 2017/0725* (2013.01); *A61B 2017/07264* (2013.01); *A61B 2017/07271* (2013.01); *A61B 2017/07278* (2013.01); *A61B 2017/07285* (2013.01); *A61B 2017/320095* (2017.08); *A61B 2017/320097* (2017.08)

(58) Field of Classification Search
CPC .. A61B 2017/00477; A61B 2017/0053; A61B 17/105
USPC ...................................................... 227/176.1
See application file for complete search history.

(56) References Cited

U.S. PATENT DOCUMENTS

| | | | |
|---|---|---|---|
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,814,055 A | 9/1998 | Knodel et al. | |
| 6,978,921 B2 | 12/2005 | Shelton, IV et al. | |
| 7,000,818 B2 | 2/2006 | Shelton, IV et al. | |
| 7,143,923 B2 | 12/2006 | Shelton, IV et al. | |
| 7,303,108 B2 | 12/2007 | Shelton, IV et al. | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,644,848 B2 | 1/2010 | Swayze et al. | |
| 7,721,930 B2 | 5/2010 | McKenna et al. | |
| 8,210,411 B2 | 7/2012 | Yates et al. | |
| 8,408,439 B2 | 4/2013 | Huang et al. | |
| 8,453,914 B2 | 6/2013 | Laurent et al. | |
| 9,186,142 B2 | 11/2015 | Fanelli et al. | |
| 9,282,962 B2 | 3/2016 | Schmid et al. | |
| 9,517,065 B2 | 12/2016 | Simms et al. | |
| 9,622,746 B2 | 4/2017 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,839,421 B2 | 12/2017 | Zerkle et al. | |
| 10,092,292 B2 | 10/2018 | Boudreaux et al. | |
| 2013/0256383 A1* | 10/2013 | Aronhalt | A61B 17/00491 227/176.1 |

* cited by examiner

SURGICAL STAPLER WITH CARTRIDGE PAN RETENTION FEATURES

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents, U.S. patent Publications, and U.S. patent applications is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
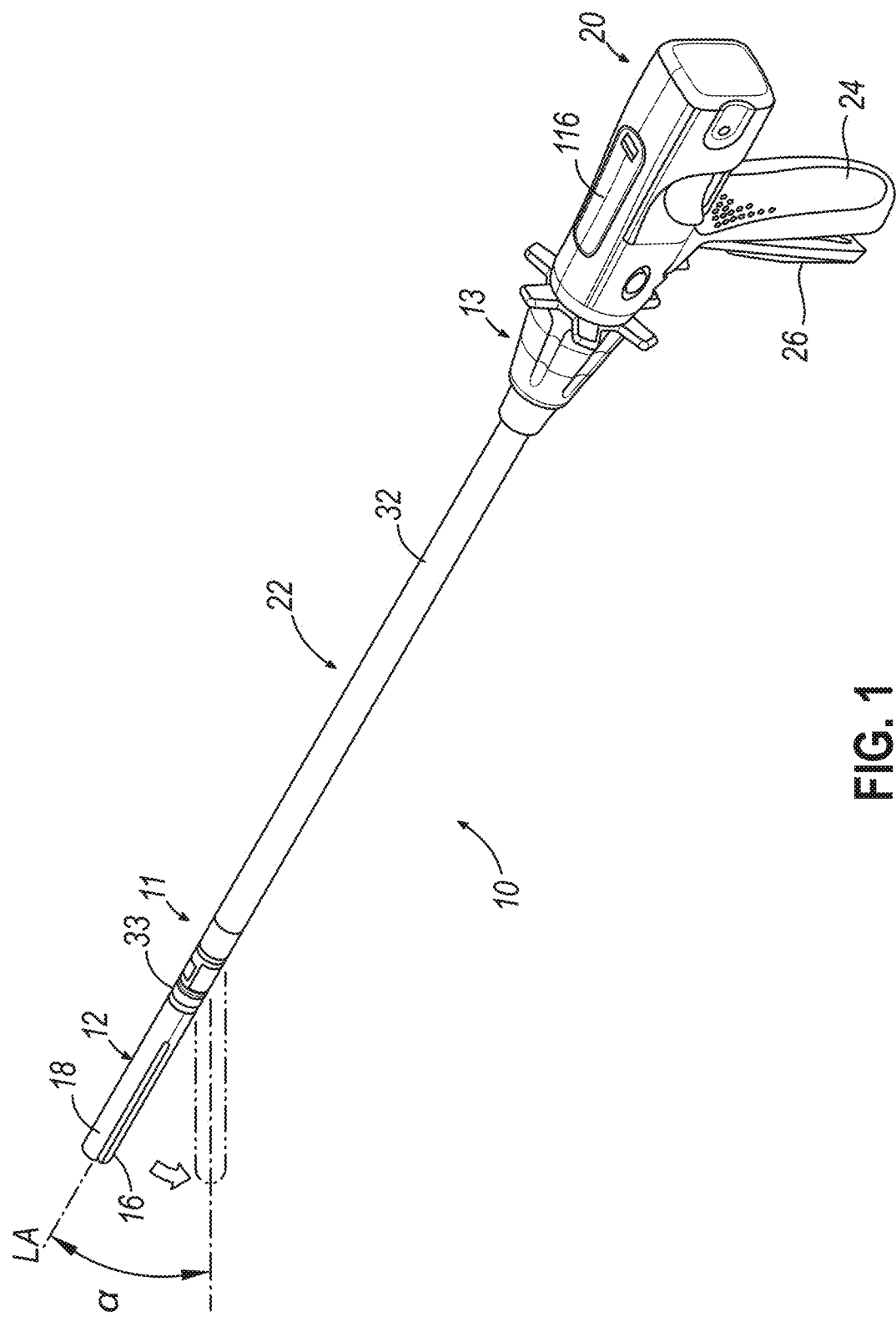
FIG. 1 depicts a perspective view of an exemplary articulating surgical stapling instrument.
Figure 2:
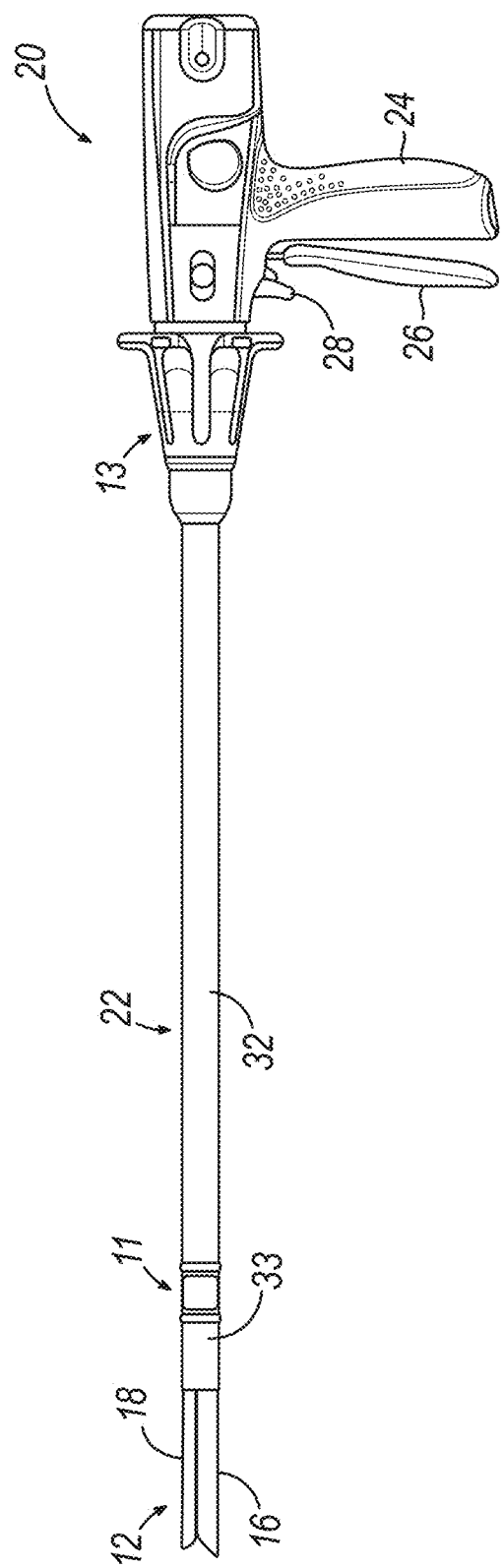
FIG. 2 depicts a side view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. EXEMPLARY SURGICAL STAPLER

FIGS. 1-7 depict an exemplary surgical stapling and severing instrument (10) that is sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, instrument (10) may be inserted directly through a thoracotomy or other type of incision. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

In some versions, shaft (22) is constructed in accordance with at least some of the teachings of U.S. Pat. No. 9,795,379, entitled "Surgical Instrument with Multi-Diameter Shaft," issued Oct. 24, 2017, the disclosure of which is incorporated by reference herein. Other suitable configurations for shaft (22) will be apparent to those skilled in the art in view of the teachings herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). End effector (12) may thereby reach behind an organ or approach tissue from a desired angle or for other reasons. In some versions, articulation joint (11) enables deflection of end effector (12) along a single plane. In some other versions, articulation joint (11) enables deflection of end effector along more than one plane. Articulation joint (11) and articulation control (13) may be configured in accordance with the teachings of any of the numerous references that are cited herein. Alternatively, articulation joint (11) and/or articulation control (13) may have any other suitable configuration. By way of example only, articulation control (13) may instead be configured as a knob that rotates about an axis that is perpendicular to the longitudinal axis (LA) of shaft (22).

In some versions, articulation joint (11) and/or articulation control (13) are/is constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein. Articulation joint (11) may also be constructed and operable in accordance with at least some of the teachings of U.S. Pat. No. 9,795,379, entitled "Surgical Instrument with Multi-Diameter Shaft," issued Oct. 24, 2017, the disclosure of which is incorporated by reference herein. Other suitable forms that articulation joint (11) and articulation control (13) may take will be apparent to those skilled in the art in view of the teachings herein.

End effector (12) of the present example includes a lower jaw (16) and an upper jaw in the form of a pivotable anvil (18). In some versions, lower jaw (16) is constructed in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Anvil (18) may be constructed in accordance with at least some of the teachings of U.S. Pat. No. 9,517,065, entitled "Integrated Tissue Positioning and Jaw Alignment Features for Surgical Stapler," issued on Dec. 13, 2016, the disclosure of which is incorporated by reference herein; at least some of the teachings of U.S. Pat. No. 9,839,421, entitled "Jaw Closure Feature for End Effector of Surgical Instrument," issued on Dec. 12, 2017, the disclosure of which is incorporated by reference herein; and/or at least some of the teachings of U.S. Pat. No. 10,092,292, entitled "Staple Forming Features for Surgical Stapling Instrument," issued Oct. 9, 2018, the disclosure of which is incorporated by reference herein. Other suitable forms that lower jaw (16) and anvil (18) may take will be apparent to those skilled in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below. Thereafter, triggers (26, 28) may be released to release the tissue from end effector (12).

FIGS. 3-6 depict end effector (12) employing an E-beam form of firing beam (14) to perform a number of functions. It should be understood that an E-beam form is just a merely illustrative example. Firing beam (14) may take any other suitable form, including but not limited to non-E-beam forms. As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing.

Some non-E-beam forms of firing beam (14) may lack upper pin (38), middle pin (46) and/or firing beam cap (44). Some such versions of instrument (10) may simply rely on closure ring (33) or some other feature to pivot anvil (18) to a closed position and hold anvil (18) in the closed position while firing beam (14) advances to the distal position. By way of example only, firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein. Other suitable forms that firing beam (14) may take will be apparent to those skilled in the art in view of the teachings herein.

Figure 3:
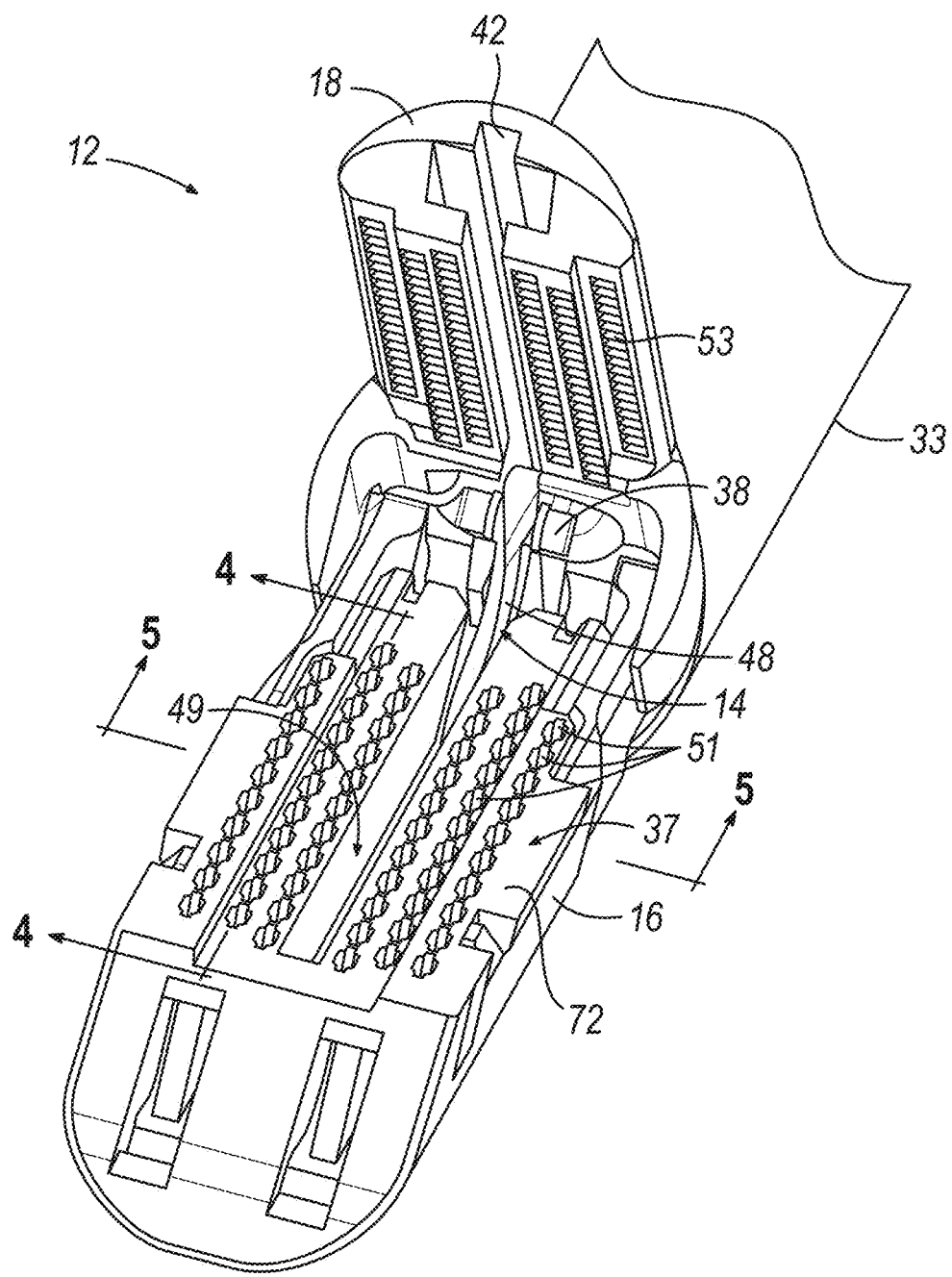
FIG. 3 depicts a perspective view of an opened end effector of the instrument of FIG. 1.
Figure 4A:
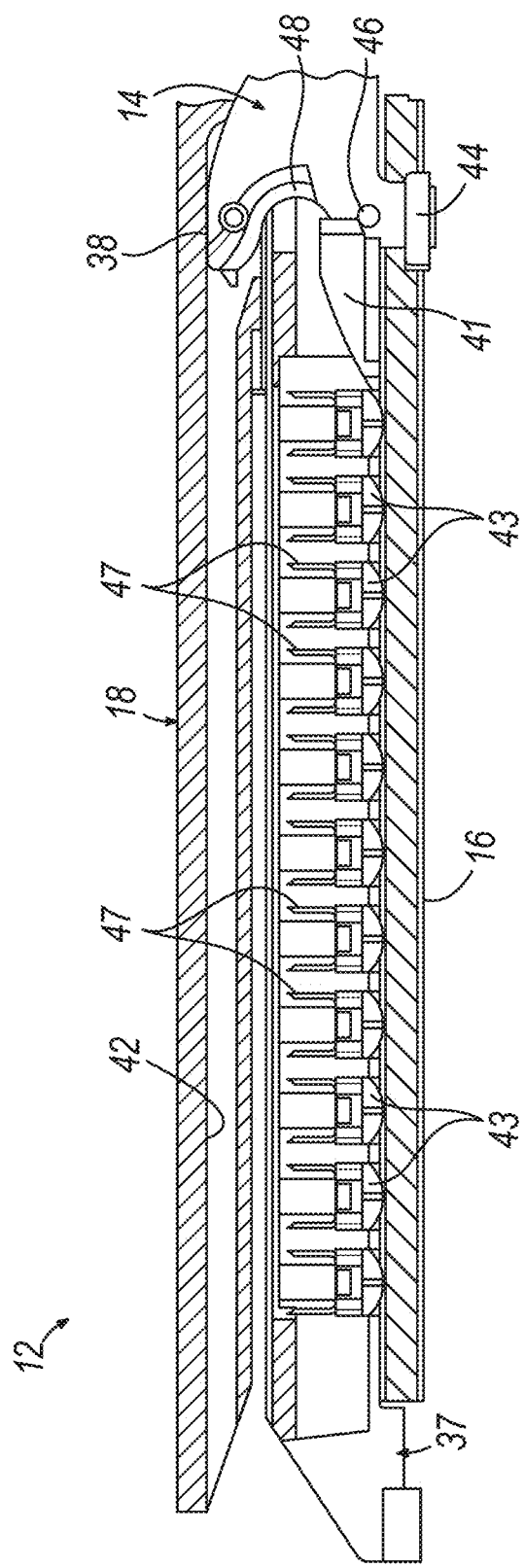
FIG. 4A depicts a side cross-sectional view of the end effector of FIG. 3, taken along line 4-4 of FIG. 3, with the firing beam in a proximal position.
Figure 4B:
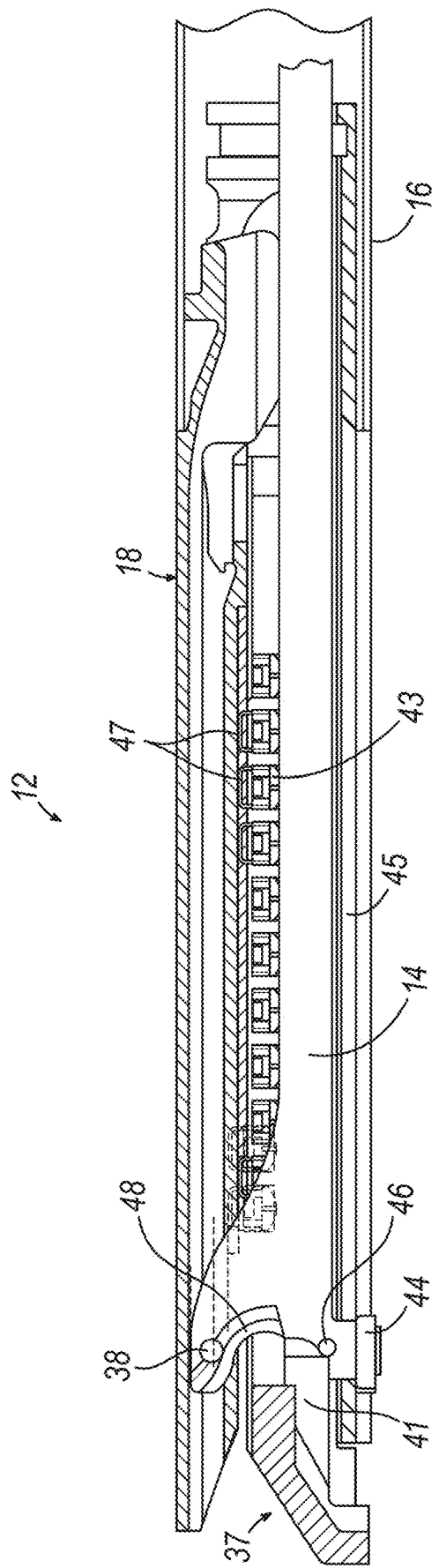
FIG. 4B depicts a side cross-sectional view of the end effector of FIG. 3, taken along line 4-4 of FIG. 3, with the firing beam in a distal position.
Figure 5:
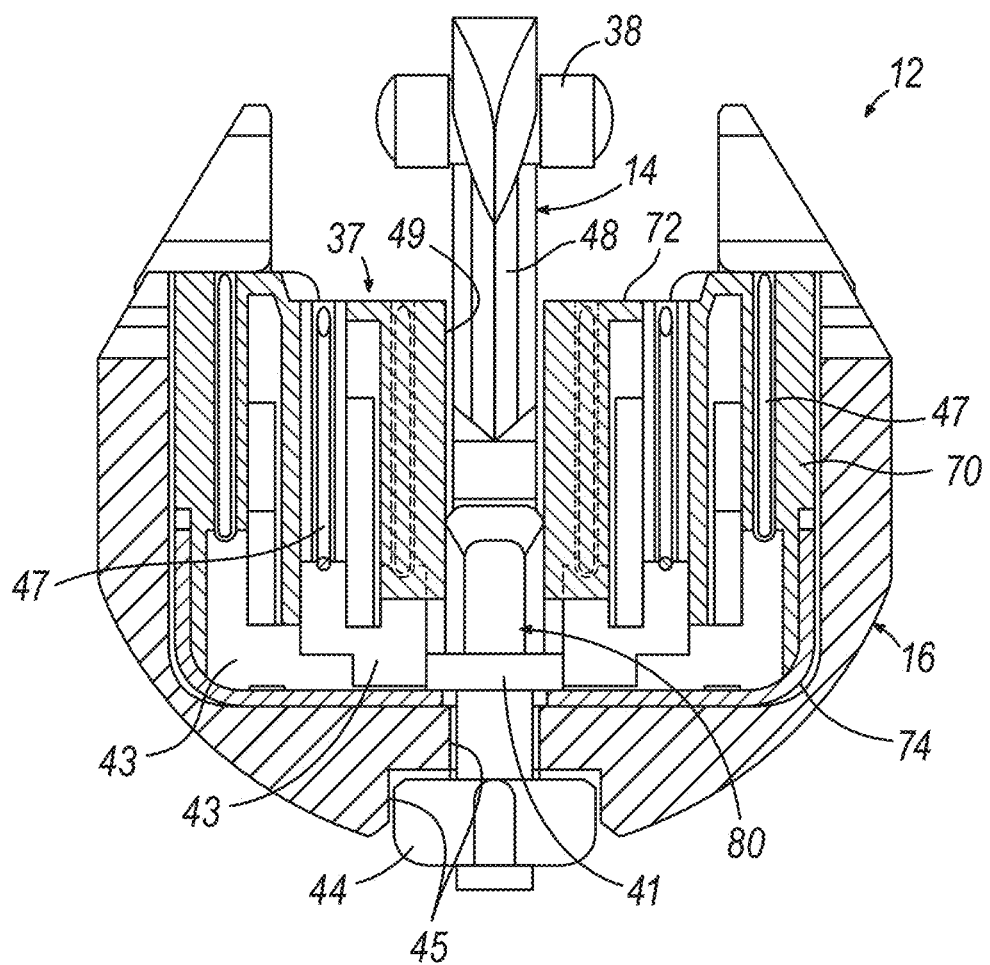
FIG. 5 depicts an end cross-sectional view of the end effector of FIG. 3, taken along line 5-5 of FIG. 3.
Figure 6:
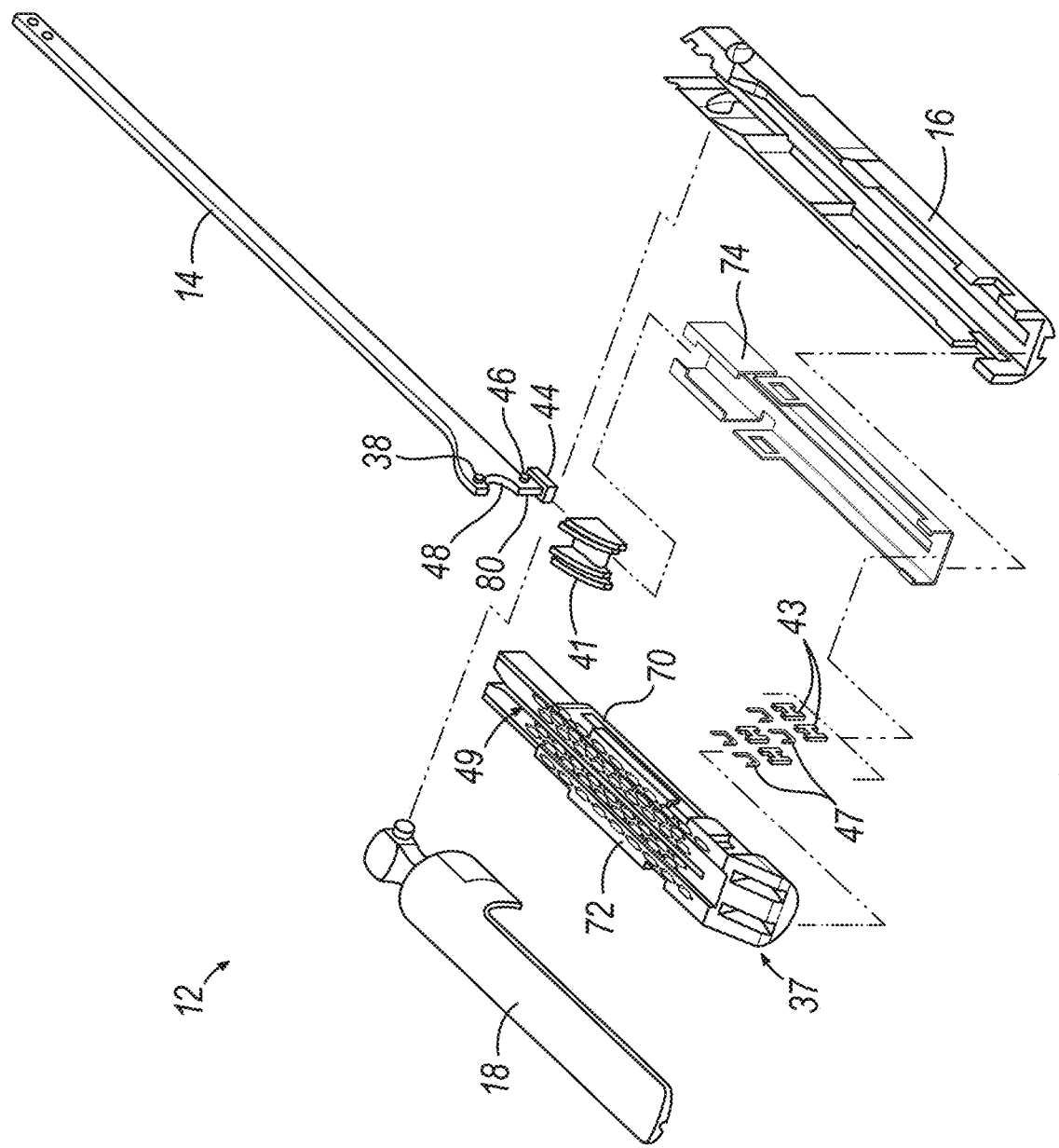
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

In some versions, staple cartridge (37) is constructed and operable in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein. In addition or in the alternative, staple cartridge (37) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Other suitable forms that staple cartridge (37) may take will be apparent to those skilled in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14), and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block

(80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
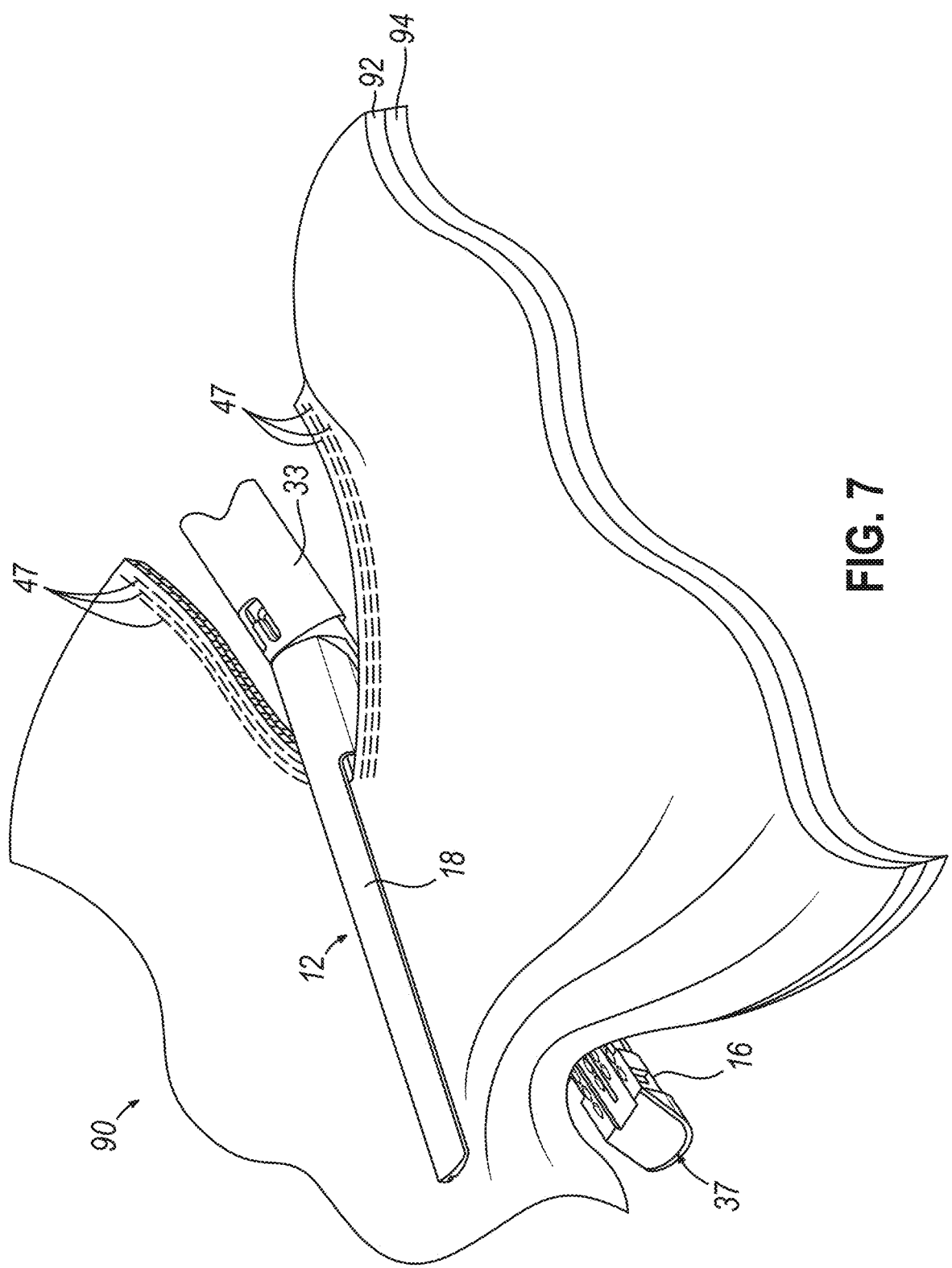
FIG. 7 depicts a perspective view of the end effector of FIG. 3, positioned at tissue and having been actuated once in the tissue.

FIG. 7 shows end effector (12) having been actuated through a single stroke through tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 7 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Furthermore, while FIG. 7 shows end effector (12) being actuated in two substantially flat, apposed planar layers (92, 94) of tissue, it should be understood that end effector (12) may also be actuated across a tubular structure such as a blood vessel, a section of the gastrointestinal tract, etc. FIG. 7 should therefore not be viewed as demonstrating any limitation on the contemplated uses for end effector (12). Various suitable settings and procedures in which instrument (10) may be used will be apparent to those skilled in the art in view of the teachings herein.

In one version, instrument (10) provides motorized control of firing beam (14). Exemplary components that may be used to provide motorized control of firing beam (14) are shown and described in U.S. Pat. No. 9,622,746, entitled "Distal Tip Features for End Effector of Surgical Instrument," issued Apr. 18, 2017, the disclosure of which is incorporated by reference herein. In addition to or in lieu of the foregoing, at least part of the motorized control may be configured in accordance with at least some of the teachings of U.S. Pat. No. 8,210,411, entitled "Motor-Driven Surgical Instrument," issued Jul. 3, 2012, the disclosure of which is incorporated by reference herein. In addition to or in lieu of the foregoing, the features operable to drive firing beam (14) may be configured in accordance with at least some of the teachings of U.S. Pat. No. 8,453,914, the disclosure of which is incorporated by reference herein; and/or in accordance with at least some of the teachings of U.S. Pat. No. 8,453,914, the disclosure of which is also incorporated by reference herein. Other suitable components, features, and configurations for providing motorization of firing beam (14) will be apparent to those skilled in the art in view of the teachings herein. It should also be understood that some other versions may provide manual driving of firing beam (14), such that a motor may be omitted. By way of example only, firing beam (14) may be actuated in accordance with at least some of the teachings of any other patent/publication reference cited herein.

Instrument (10) may also include a lockout switch and lockout indicator as shown and described in U.S. Pat. No. 9,622,746, entitled "Distal Tip Features for End Effector of Surgical Instrument," issued Apr. 18, 2017, the disclosure of which is incorporated by reference herein. Additionally, a lockout switch and/or lockout indication and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Instrument (10) also include a manual return switch (116) configured to act as a "bailout" feature, enabling the operator to quickly begin retracting firing beam (14) proximally during a firing stroke. In other words, manual return switch (116) may be manually actuated when firing beam (14) has only been partially advanced distally. Manual return switch (116) may provide further functionality in accordance with at least some of the teachings of U.S. Pat. No. 9,622,746, entitled "Distal Tip Features for End Effector of Surgical Instrument," issued Apr. 18, 2017, the disclosure of which is incorporated by reference herein.

In describing the operation of instrument (10), use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition or in the alternative, the pivot axis may slide along the slot/channel first, with anvil (18) then pivoting about the pivot axis after the pivot axis has slid a certain distance along the slot/channel. It should be understood that such sliding/translating pivotal movement is encompassed within terms such as "pivot," "pivots," "pivotal," "pivotable," "pivoting," and the like. Of course, some versions may provide pivotal movement of anvil (18) about an axis that remains fixed and does not translate within a slot or channel, etc.

It should be understood that instrument (10) may be configured and operable in accordance with any of the teachings of U.S. Pat. Nos. 4,805,823; 5,415,334; 5,465,895; 5,597,107; 5,632,432; 5,673,840; 5,704,534; 5,814,055; 6,978,921; 7,000,818; 7,143,923; 7,303,108; 7,367,485; 7,380,695; 7,380,696; 7,404,508; 7,434,715; 7,721, 930; 8,408,439; and/or 8,453,914. As noted above, the disclosures of each of those patents and publications are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents/publications cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those skilled in the art in view of the teachings herein.

II. STAPLE CARTRIDGE WITH PROXIMAL FASTENING FEATURES

As noted above, end effector (12) of instrument is configured to receive staple cartridge (37). The distal end of firing beam (14) may then be received in the proximal end of staple cartridge (37) to drive wedge sled (41) and cutting edge (48) distally within staple cartridge (37) to contemporaneously sever tissue (90) and drive staples (47) upwardly to seal tissue (90). Thus, it should be understood that alignment between staple cartridge (37) and firing beam (14) is desirable to promote properly driven staples (47) and severing of tissue (90).

However, under some circumstances, certain portions of staple cartridge (37) may become misaligned relative to each other during packaging, shipping, and/or handling of staple cartridge (37). For instance, in some circumstances, portions of cartridge body (70) may become misaligned relative to corresponding portions of lower cartridge tray (74). In such circumstances, challenges may arise with driving firing beam (14) distally within staple cartridge (37). It should be therefore understood that in some examples, versions of a staple cartridge similar to staple cartridge (37) may be desirable that incorporate features to promote secure fastening between various components of staple cartridge (37), thereby promoting consistent and reliable alignment between components of staple cartridge (37). Although various suitable fastening features are described herein in specific configurations and in combination with specific devices, it should be understood that in other examples such fastening features arranged in other configurations and with other devices.

Figure 8:
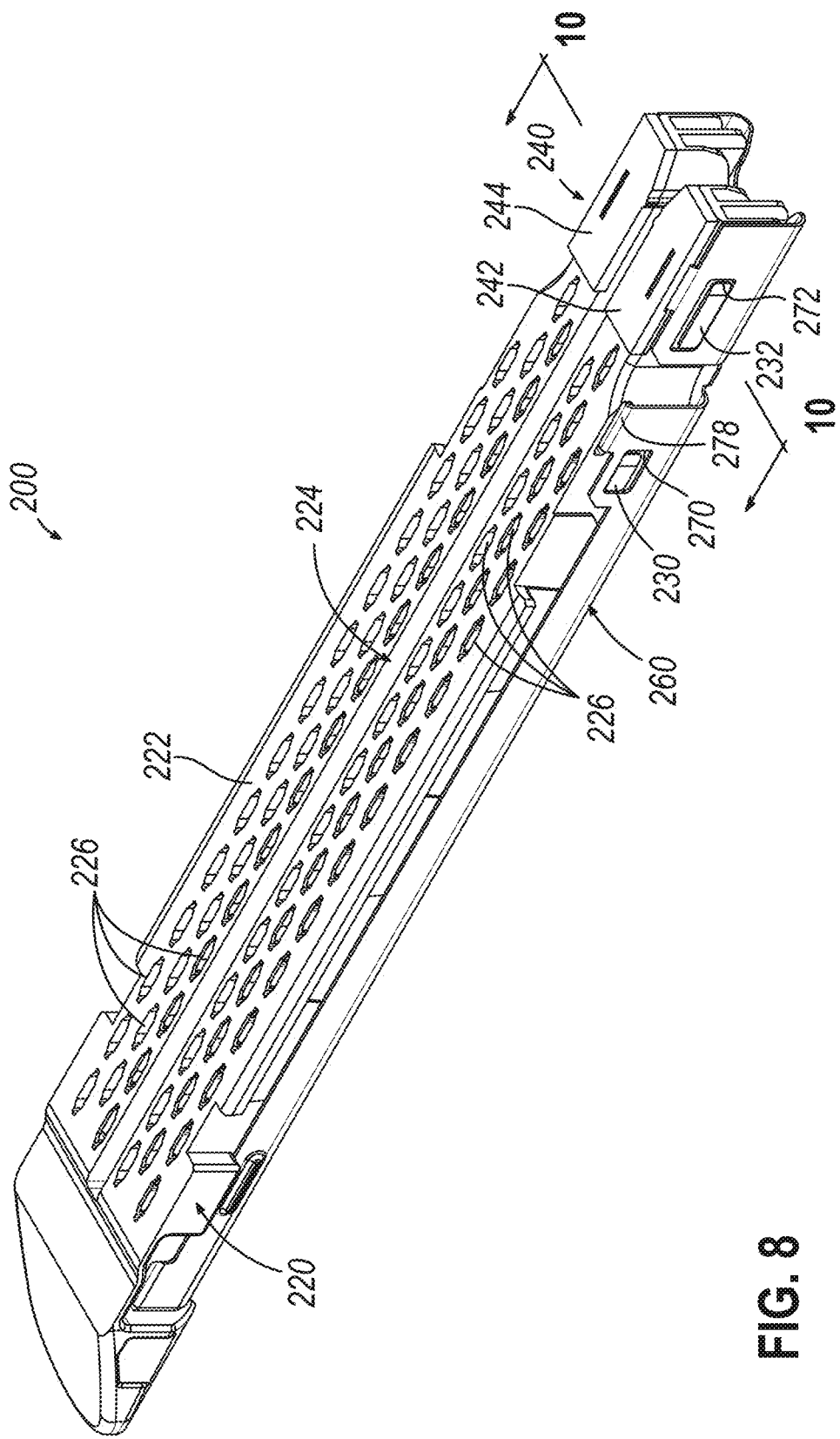
FIG. 8 depicts a perspective view of an exemplary staple cartridge for use with the instrument of FIG. 1.
Figure 9:
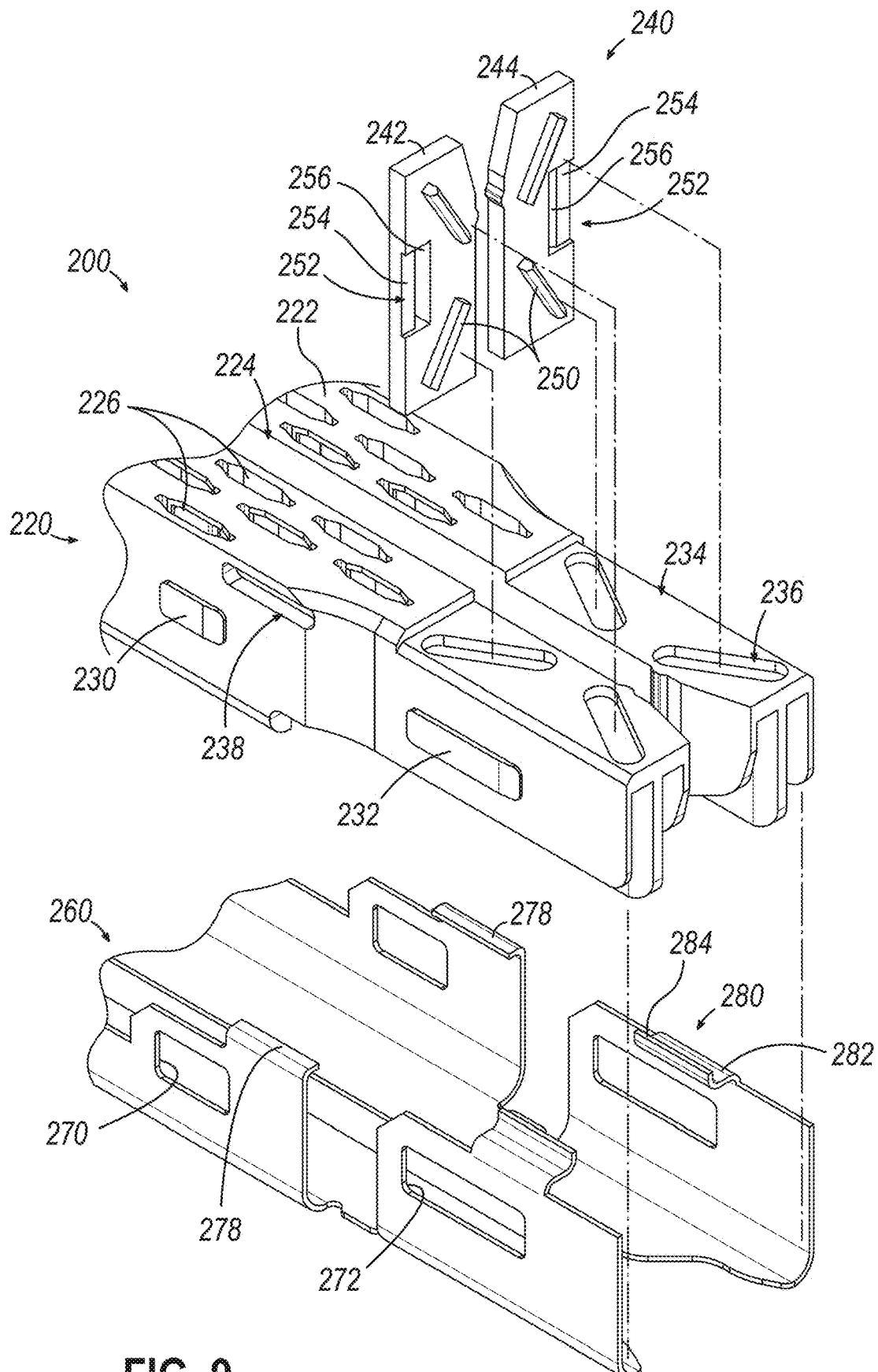
FIG. 9 depicts an enlarged, perspective view of a proximal end of the staple cartridge of FIG. 8.
Figure 10:
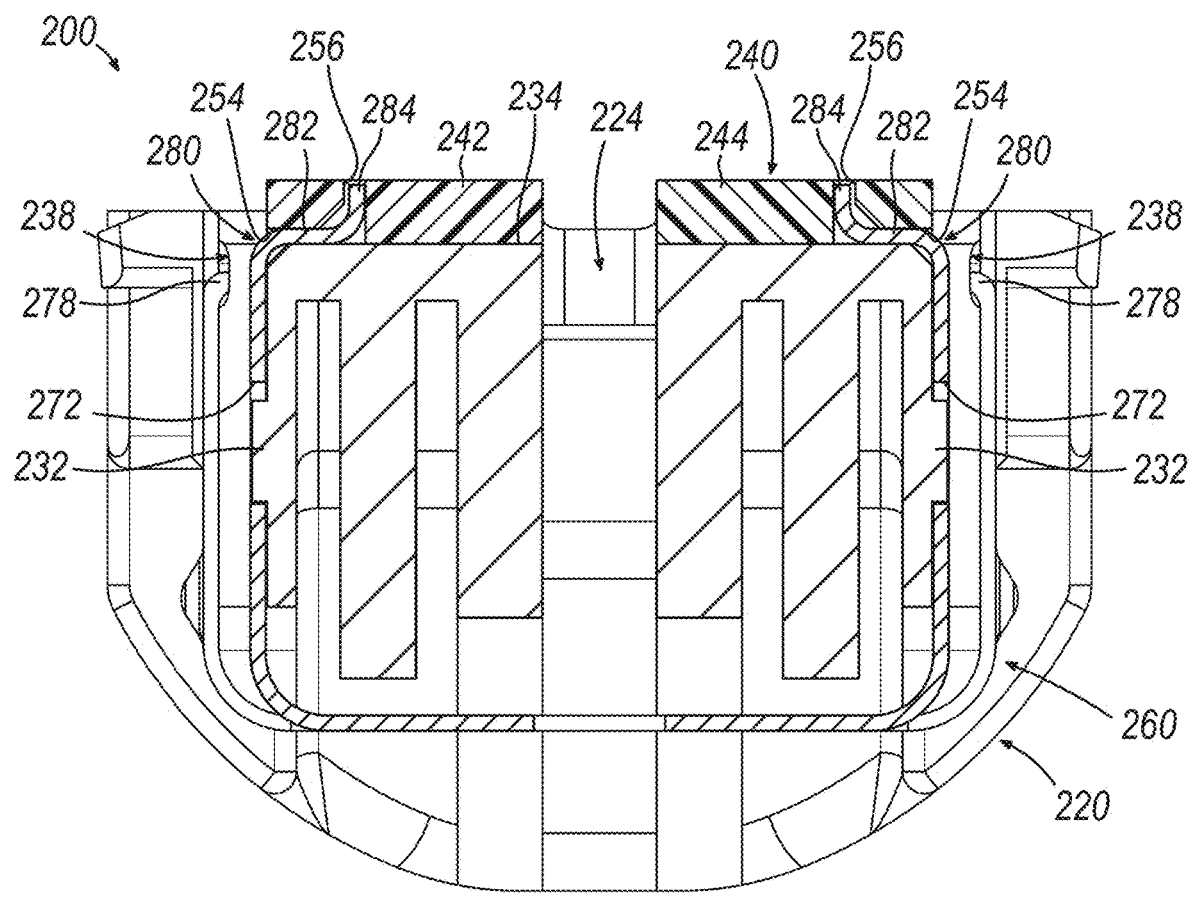
FIG. 10 depicts a rear cross-sectional view of the proximal end of the staple cartridge of FIG. 8, the cross-section taken along line 10-10 of FIG. 8.

FIGS. 8-10 show an exemplary alternative staple cartridge (200) that is configured for use with instrument (10) described above in lieu of staple cartridge (37). Unless otherwise described herein, it should be understood that staple cartridge (200) is substantially similar to staple cartridge (37) described above. For instance, as with staple cartridge (37), staple cartridge (200) of this example includes a cartridge body (220). As similarly discussed above, cartridge body (220) defines an upper deck (222) and is coupled to a lower cartridge tray (260). Upper deck (222) at least partially defines a vertical slot (224) that is formed through part of staple cartridge (200). Upper deck (222) further defines three rows of staple apertures (226) extending through upper deck (222) on one side of vertical slot (224), with another set of three rows of staple apertures (226) being formed through upper deck (222) on the other side of vertical slot (224). Of course, any other suitable number of staple rows (e.g., two rows, four rows, any other number) may be provided.

It should be understood that, like with staple cartridge (37), staple cartridge (200) of the present example is configured for use with wedge sled (41) and firing beam (14) to drive a plurality of staple drivers (not shown). The staple drivers may be captured between cartridge body (220) and tray (260), with wedge sled (41) being located proximal to the staple drivers. Wedge sled (41) is movable longitudinally within staple cartridge (200); while the staple drivers are movable vertically within staple cartridge (200). Staples (not shown) may also be positioned within cartridge body (220), above corresponding staple drivers. Each staple may thus be driven vertically within cartridge body (220) by a corresponding staple driver to drive the staple out through an associated staple aperture (226).

Staple cartridge (200) of this example includes certain features configured to promote firm retention and alignment between cartridge body (220) and cartridge tray (260). As will be discussed in further detail below, such retention features are generally positioned near the proximal end of staple cartridge (200). This proximal positioning may be generally desirable because movable components of instrument (10) such as firing beam (140) engage directly with the proximal end of staple cartridge (200). Thus, proper alignment between cartridge body (220) and cartridge tray (260) is particularly desirable at the proximal end of staple cartridge (200).

As best seen in FIG. 9, each side of cartridge body (220) includes a distal laterally-extending protrusion (230) and a proximal laterally-extending protrusion (232). Protrusions (230, 232) are generally configured to be received within corresponding windows (270, 272) of cartridge tray (260) to thereby provide a snap-fit configuration between cartridge body (220) and cartridge tray (260).

Each protrusion (230, 232) extends outwardly from a side surface of cartridge body (220) and defines generally rectangular shape with rounded corners. The outward extension of each protrusion (230, 232) generally corresponds to the thickness of cartridge tray (260). As will be described in greater detail below, this particular outward extension may be desirable to promote a generally flat or flush side surface of staple cartridge (200) when cartridge body (220) and cartridge tray (260) are coupled together.

Cartridge tray (260) correspondingly defines a distal window (270) and a proximal window (272) in each side thereof. Each window (270, 272) is configured as a generally rectangular cutout in each side of cartridge tray (260). Thus, each window (270, 272) is configured to receive a corresponding protrusion (230, 232) of cartridge body (220). Although the particular shape of protrusions (230, 232) and windows (270, 272) is shown as being generally rectangular in the present example, it should be understood that in other examples, various alternative shapes may be used. For instance, in some examples, protrusions (230, 232) and windows (270, 272) may be oval-shaped or circular. In other examples, protrusions (230, 232) and windows (270, 272) may be triangular, square, or any other suitable shape. Regardless of shape, it should be understood that an additional number of protrusion (230, 232) and window (270, 272) combinations may be used along the length of staple cartridge (200).

Cartridge body (220) further includes a side-pocket (238), indentation, or opening on each side of cartridge body (220). Side-pocket (238) is generally configured to receive a corresponding feature of cartridge tray (260) to securely fasten cartridge body (220) to cartridge tray (260). In the present example, side-pocket (238) is configured as a rectangular opening in the side of cartridge body (220). Of course, various other suitable shapes may be used, as will be described in greater detail below. Side-pocket (238) of the present example extends through cartridge body (220) from an exterior surface into an interior cavity of cartridge body (220). Thus, side-pocket (238) of the present example is a through hole. Alternatively, it should be understood that in other examples, side-pocket (238) may extend through only a portion of cartridge body (220) similar to a recess, a groove, or a blind bore.

Cartridge tray (260) further includes a distal tab (278) on each side corresponding to each side-pocket (238) of cartridge body (220). Each distal tab (278) is configured to be received within side-pocket (238) of cartridge body (220) to securely fasten cartridge body (220) to cartridge tray (260). Each distal tab (278) defines an inverted L-shape. Thus, each distal tab (278) includes an approximately 90° bend followed by an inward extension. The particular length of the inward extension for each distal tab (278) may be any suitable amount to promote coupling between cartridge body (220) and cartridge tray (260). For instance, in some examples, the inward extension of each distal tab (278) corresponds to the approximate wall thickness of cartridge body (220). The extension of each distal tab (278) may be configured to hold cartridge body (220) to lower cartridge tray (260) and thus prevent lateral or upward movement of cartridge body (220).

Cartridge body (220) further includes a retention cap (240). Retention cap (240) of the present example is generally configured to fasten to a portion of cartridge body (220) to trap at least a portion of lower cartridge tray (260) within cartridge body (220). As best seen in FIG. 9, cartridge body (220) defines a proximal recess (234) that is configured to receive retention cap (240). The particular depth of proximal recess (234) is configured to provide a generally smooth transition between the surface of upper deck (222) and the surface of retention cap (240). As will be discussed in greater detail below, this transition may be at least partially dictated by the thickness of retention cap (240).

Retention cap (240) of the present example is separated into a left side portion (242) and a right side portion (244) such that retention cap (240) may at least partially define vertical slot (224) when fastened to cartridge body (220). Each side portion (242, 244) is generally a mirror image of the other and is thus symmetrical. However, it should be understood that in other examples, some asymmetry may be present.

Retention cap (240) generally forms a square shape with vertical slot (224) extending through the center thereof. Thus, each side portion (242, 244) generally defines a rectangular shape. The thickness of each side portion (242, 244) is generally configured to support a mating arrangement with various components of cartridge body (220) and lower cartridge tray (260). Various suitable thicknesses for each side portion (242, 244) will be described in greater detail below.

As discussed above, retention cap (240) is configured to be securely fastened within proximal recess (234) of cartridge body (220). In the present example, retention cap (240) is configured for fastening by ultrasonic welding. In other examples, it should be understood that various alternative fastening means may be used such as adhesive bonding, mechanical fastening, and/or using any other suitable components or techniques.

To promote robust ultrasonic welds between retention cap (240) and cartridge body (220), retention cap (240) includes a plurality of energy directors (250). Each energy director (250) is configured to engage a corresponding feature of cartridge body (220) to thereby concentrate ultrasonic energy or vibration provided by a sonotrode during welding into a predetermined area or at a predetermined point. In the present example, each side portion (242, 244) includes two energy directors (250). Each energy director (250) protrudes downwardly from a bottom surface of each side portion (242, 244) to mate with a corresponding energy well (236) defined within proximal recess (234) of cartridge body (220).

Each energy director (250) of the present example defines a generally rectangular cross-sectional shape extending downwardly from the bottom surface of each side portion (242, 244). In addition, the end of each energy director (250) is chamfered or tapered to an edge or substantial edge. Thus, it should be understood that the edge of each energy director (250) forms a substantially triangular shape. In some examples, this edge configuration is generally desirable to promote the concentration of ultrasonic energy at the tip of each energy director (250). For instance, with an edge (or substantial edge), the edge will concentrate the highest stress during welding. Thus, melting during welding will occur initially at the edge, thereby providing greater control over the location of melting and the ultimate amount of material melted during ultrasonic welding.

Each energy director (250) is positioned at an orientation to generally promote uniform welding. As can be seen, each energy director (250) begins at a respective outer corner of a corresponding side portion (242, 244) and then extends inwardly toward the centerline of each side portion (242, 244). This orientation is configured to provide uniform weld coverage across the mating surfaces between cartridge body (220) and retention cap (240).

As noted above, proximal recess (234) includes a plurality of energy wells (236) corresponding to each energy director (250). In the present example, each energy well (236) forms an elongate indentation in the upper surface of cartridge body (220) defined by proximal recess (234). Because each energy well (236) is configured to receive a corresponding energy director (250), each energy well (236) has an orientation that corresponds to a corresponding energy director (250). In addition, it should be understood that the depth of each energy well (236) is undersized relative to the downward extension of each energy director (250). This undersized depth permits at least some of each energy director (250) to be melted during ultrasonic welding before the mating surfaces between cartridge body (220) and retention cap (240) contact each other.

Although various specific configurations for energy directors (250) and energy wells (236) are described herein, various alternative configurations may be used in other examples. For instance, in some examples, energy directors (250) may be associated with proximal recess (234), while energy wells (236) may be associated with retention cap (240). In addition, or in the alternative, it should be understood that energy directors (250) (and correspondingly, energy wells (236) may take on a variety of shapes, forms, and orientations. For instance, although the present example includes four energy directors (250), in other examples any other suitable number of energy directors may be used (e.g., six, eight, or ten). Similarly, the length and orientation of each energy director (250) may be varied. For instance, in other examples, each energy director (250) may be oriented axially rather than being at an angle. In addition, or in the alternative, the combined energy directors (250) may be positioned in a linear array (e.g., rows/columns). Still other suitable alternative configurations for energy directors (250) and energy wells (236) will be apparent to those skilled in the art in view of the teachings herein.

Although the present example shows energy directors (250) and energy wells (236) being used in connection with the proximal end of cartridge body (220), it should be understood that in other examples substantially similar features could be used on other parts of cartridge body (220). Moreover, in still other examples features substantially similar to energy directors (250) and energy wells (236) may be used in other portions of instrument (10) described herein or in other instruments entirely. Suitable alternative instruments may include, by way of example only, other instruments having small mating parts where secure fastening is desirable for adequate performance.

Each side portion (242, 244) further includes a tab receiver (252) extending through a portion of each side portion (242, 244). As will be described in greater detail below, each tab receiver (252) is generally configured to receive and capture a portion of lower cartridge tray (260) to securely fasten lower cartridge tray (260) to cartridge body (220). Each tab receiver (252) includes a horizontal channel (254) and a vertical channel (256) to form a generally L-shaped configuration within each side portion (242, 244). As best seen in FIG. 9, horizontal channel (254) extends from the outer side of each side portion (242, 244) inwardly towards the center thereof. Horizontal channel (254) is also formed as a rectangular cutout in the bottom surface of each side portion (242, 244). As will be described in greater detail below, this configuration of horizontal channel (254) is generally configured to accommodate a horizontal extension of lower cartridge tray (260) between a respective side portion (242, 244) and cartridge body (220).

Vertical channel (256) extends upwardly from horizontal channel (254) through the entire thickness of a respective side portion (242, 244). As with horizontal channel (254), vertical channel (256) defines a generally rectangular shape. However, unlike horizontal channel (254), vertical channel (256) is generally configured to accommodate a vertical extension of lower cartridge tray (260) to prevent lateral or side-to-side movement of cartridge tray (260) relative to cartridge body (220).

Lower cartridge tray (260) further includes a proximal tab (280) on each side thereof. Each proximal tab (280) is generally configured for receipt within tab receiver (252) of each side portion (242, 244). Thus, it should be understood that each proximal tab (280) has a cooperative relationship with a respective tab receiver (252) to capture lower cartridge tray (260) between cartridge body (220) and retention cap (240).

As best seen in FIG. 9, proximal tab (280) includes a horizontal extension (282) and a vertical extension (284). Together, horizontal extension (282) and vertical extension (284) are rounded to form a generally S-shaped pattern. As best seen in FIG. 10, when retention cap (240) is fastened to cartridge body (220), horizontal extension (282) is configured for receipt within horizontal channel (254) of a respective tab receiver (252). Meanwhile, vertical extension (284) is configured for receipt within vertical channel (256) of a respective tab receiver (252). As such, it should be understood that horizontal extension (282) secures the vertical or up-and-down orientation of lower cartridge tray (260) relative to cartridge body (220). Meanwhile, vertical extension (284) secures the lateral or side-to-side orientation of lower cartridge tray (260) relative to cartridge body (220).

In some examples, it may be desirable to have a predetermined relationship between the thickness of retention cap (240), the length of vertical extension (284) of proximal tab (280), and the depth of proximal recess (234). For instance, in the present example, the thickness of retention cap (240) generally corresponds to the length of vertical extension (284) to promote a flush fit or slightly indented fit between the upper end of vertical extension (284) and the upper surface of retention cap (240). Such a configuration may be generally desirable to prevent interference of proximal tab (280) with operation of instrument (10). In other examples, this relationship may also be configured to correspond to the depth of proximal recess (234) such that all of upper deck (222), the upper end of vertical extension (284), and the upper surface of retention cap (240) are aligned along a planar surface. Of course, in other examples, the thickness of retention cap (240) may be slightly oversized relative to the depth of proximal recess (234), as shown in the present example.

III. EXEMPLARY STAPLE CARTRIDGE WITH DISTORTED PORTION

Figure 11:
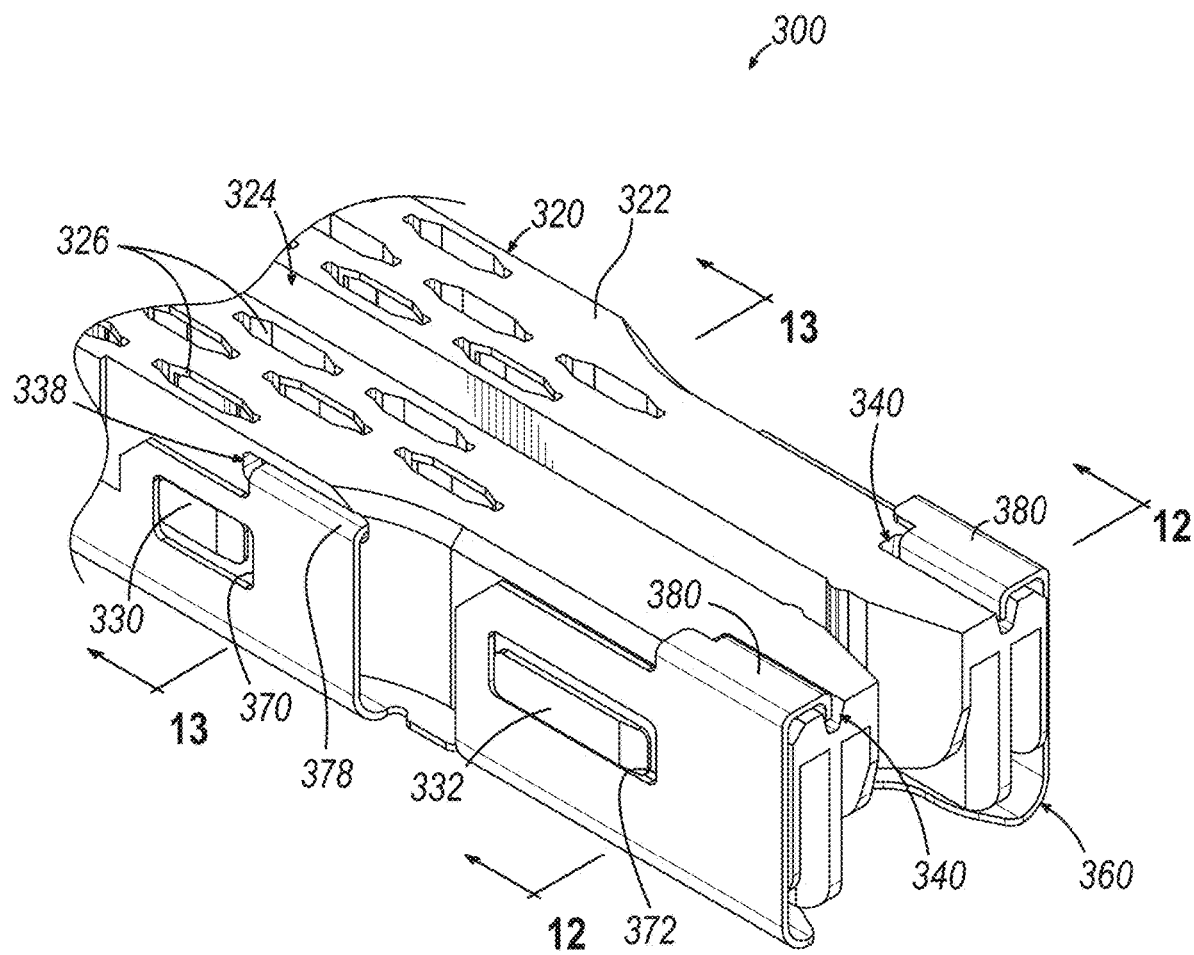
FIG. 11 depicts a perspective view of a proximal end of another exemplary staple cartridge for use with the instrument of FIG. 1.

FIG. 11 shows an exemplary alternative staple cartridge (300) that is configured for use with instrument (10) described above in lieu of staple cartridge (37). Unless otherwise described herein, it should be understood that staple cartridge (300) is substantially similar to staple cartridges (37, 200) described above. For instance, as with staple cartridge (37), staple cartridge (300) of this example includes a cartridge body (320). As similarly discussed above, cartridge body (320) defines an upper deck (322) and is coupled to a lower cartridge tray (360). Upper deck (322) at least partially defines a vertical slot (324) that is formed through part of staple cartridge (300). Upper deck (322) further defines three rows of staple apertures (326) extending through upper deck (322) on one side of vertical slot (324), with another set of three rows of staple apertures (326) being formed through upper deck (322) on the other side of vertical slot (324). Of course, any other suitable number of staple rows (e.g., two rows, four rows, any other number) may be provided.

It should be understood that, like with staple cartridge (37), staple cartridge (300) of the present example is configured for use with wedge sled (41) and firing beam (14) to drive a plurality of staple drivers (not shown). The staple drivers may be captured between cartridge body (320) and tray (360), with wedge sled (41) being located proximal to the staple drivers. Wedge sled (41) is movable longitudinally within staple cartridge (300); while the staple drivers are movable vertically within staple cartridge (300). Staples (not shown) may also be positioned within cartridge body (320), above corresponding staple drivers. Each staple may thus be driven vertically within cartridge body (320) by a corresponding staple driver to drive the staple out through an associated staple aperture (326).

As with staple cartridge (200) described above, staple cartridge (300) of this example includes certain features configured to promote firm retention and alignment between cartridge body (320) and cartridge tray (360). As similarly discussed above, such retention features are generally positioned near the proximal end of staple cartridge (300). This proximal positioning may be generally desirable because movable components of instrument (10) such as firing beam (14) engage directly with the proximal end of staple cartridge (300). Thus, proper alignment between cartridge body (320) and cartridge tray (360) is particularly desirable at the proximal end of staple cartridge (300).

As best seen in FIG. 11, cartridge body (320) is similar to cartridge body (220) in that each side of cartridge body (320) includes a distal laterally-extending protrusion (330) and a proximal laterally-extending protrusion (332). Protrusions (330, 332) are generally configured to be received within corresponding windows (370, 372) of cartridge tray (360) to thereby provide a snap-fit configuration between cartridge body (320) and cartridge tray (360).

As with protrusions (230, 232) described above, each protrusion (330, 332) extends outwardly from a side surface of cartridge body (320) and defines generally rectangular shape with rounded corners. The outward extension of each protrusion (330, 332) generally corresponds to the thickness of cartridge tray (360). As will be described in greater detail below, this particular outward extension may be desirable to promote a generally flat or flush side surface of staple cartridge (300) when cartridge body (320) and cartridge tray (360) are coupled together.

Cartridge tray (360) correspondingly defines a distal window (370) and a proximal window (372) in each side thereof. Each window (370, 372) is configured as a generally rectangular cutout in each side of cartridge tray (360). Thus, each window (370, 372) is configured to receive a corresponding protrusion (330, 332) of cartridge body (320). Although the particular shape of protrusions (330, 332) and windows (370, 372) is shown as being generally rectangular in the present example, it should be understood that in other examples, various alternative shapes may be used. For instance, in some examples, protrusions (330, 332) and windows (370, 372) may be oval-shaped or circular. In other examples, protrusions (330, 332) and windows (370, 372) may be triangular, square, or any other suitable shape. Regardless of shape, it should be understood that an additional number of protrusion (330, 332) and window (370, 372) combinations may be used along the length of staple cartridge (300).

Cartridge body (320) further includes a side-pocket (338), indentation, or opening on each side of cartridge body (320). Side-pocket (338) is generally configured to receive a corresponding feature of cartridge tray (360) to securely fasten cartridge body (320) to cartridge tray (360). In the present example, side-pocket (338) is configured as a rectangular opening in the side of cartridge body (320). Of course, various other suitable shapes may be used, as will be described in greater detail below. Side-pocket (338) of the present example extends through cartridge body (320) from an exterior surface into an interior cavity of cartridge body (320). Thus, side-pocket (338) of the present example is a through hole. Alternatively, it should be understood that in other examples, side-pocket (338) may extend through only a portion of cartridge body (320) similar to a recess, a groove, or a blind bore.

Cartridge tray (360) further includes a distal tab (378) on each side corresponding to each side-pocket (338) of cartridge body (320). Each distal tab (378) is configured to be received within side-pocket (338) of cartridge body (320) to securely fasten cartridge body (320) to cartridge tray (360). Each distal tab (378) defines an inverted L-shape. Thus, each distal tab (378) includes an approximately 90° bend followed by an inward extension. The particular length of the inward extension for each distal tab (378) may be any suitable amount to promote coupling between cartridge body (320) and cartridge tray (360). For instance, in some examples, the inward extension of each distal tab (378) corresponds to the approximate wall thickness of cartridge body (320). The extension of each distal tab (378) may be configured to hold cartridge body (320) to lower cartridge tray (360) and thus prevent lateral or upward movement of cartridge body (320).

Unlike staple cartridge (200) described above, staple cartridge (300) of the present examples omits certain features similar to retention cap (240) described above. Instead, staple cartridge (300) of the present example includes certain fastening features combined with various methods of manipulation to securely fasten cartridge body (320) to lower cartridge tray (360). As best seen in FIG. 11, cartridge body (320) includes a pair of proximal channels (340) positioned on each side of on the proximal end thereof. Each proximal channel (340) extends downwardly from upper deck (322) into the surface of cartridge body (320) and extends longitudinally along a portion of the length of cartridge body (320). Additionally, each proximal channel (340) is inwardly offset by a predetermined amount from a respective side of cartridge body (320). As will be described in greater detail below, each proximal channel (340) is configured to receive a corresponding retention feature of lower cartridge tray (360).

Lower cartridge tray (360) includes a proximal tab (380) on each side thereof. Each proximal tab (380) corresponds to each proximal channel (340) of cartridge body (320). As such, at least a portion of each proximal tab (380) is configured for receipt within a respective proximal channel (340). Each proximal tab (380) includes a double-fold to define a 270° bend. This bend defines a structure similar to a three-sided box. In other words, each proximal tab (380) first extends horizontally and inwardly from the side of lower cartridge tray (360) at about a 90° angle relative to the side of lower cartridge tray (360). Each proximal tab (380) then bends about another 90° and extends downwardly.

As can be seen in FIG. 11, each proximal tab (380) is received within a respective proximal channel (340) of cartridge body (320) when cartridge body (320) and lower cartridge tray (360) are coupled together. As can be seen, a portion of each proximal tab (380) extends over the surface of upper deck (322) for about the inward offset distance of each proximal channel (340) from the side of cartridge body (320). This horizontal extension of each proximal tab (380) is configured to hold cartridge body (320) within lower cartridge tray (360) along the vertical or up-down plane or axis. Each proximal tab (380) then bends downwardly, extending into a respective proximal channel (340). This vertical extension of each proximal tab (380) is configured to hold cartridge body (320) within lower cartridge tray (360) along the horizontal or side-to-side plane or axis. Thus, it should be understood that the relationship between proximal tabs (380) and proximal channels (340) is configured to maintain the position of cartridge body (320) relative to lower cartridge tray (360) along at least 2-axis.

Figure 12A:
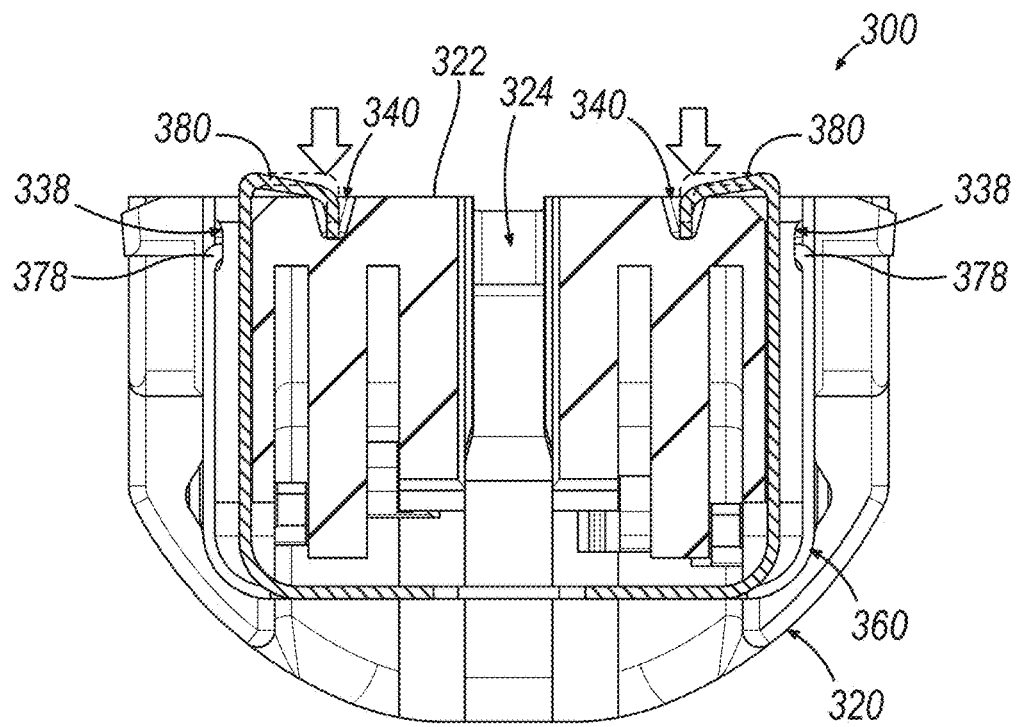
FIG. 12A depicts a rear cross-sectional view of the staple cartridge of FIG. 11, the cross-section taken along line 12-12 of FIG. 11, according to one example of an assembly method.

In some examples, further fastening means may be desirable to more firmly hold cartridge body (320) in position relative to lower cartridge tray (360). In some examples, additional manipulation of lower cartridge tray (360) may be performed after cartridge body (320) and lower cartridge tray (360) are coupled together to increase the robustness of the coupling thereof. For instance, as can be seen in FIG. 12A, each proximal tab (380) may be manipulated after coupling to deform each proximal tab (380). In the present example, this deformation involves applying a downward force onto the top of each proximal tab (380) until each proximal tab (380) is deformed. In the present example, this force is applied by peening each proximal tab (380) at one or more locations along the upper portion thereof. By way of example only, this process of peening each proximal tab (380) may create a series of dimples, indentations, or divots in the surface thereof to increase engagement between proximal tab (380) and cartridge body (320). In other examples, the force may be applied by other suitable means such as a press or any other suitable means as will be apparent to those skilled in the art in view of the teachings herein.

Figure 12B:
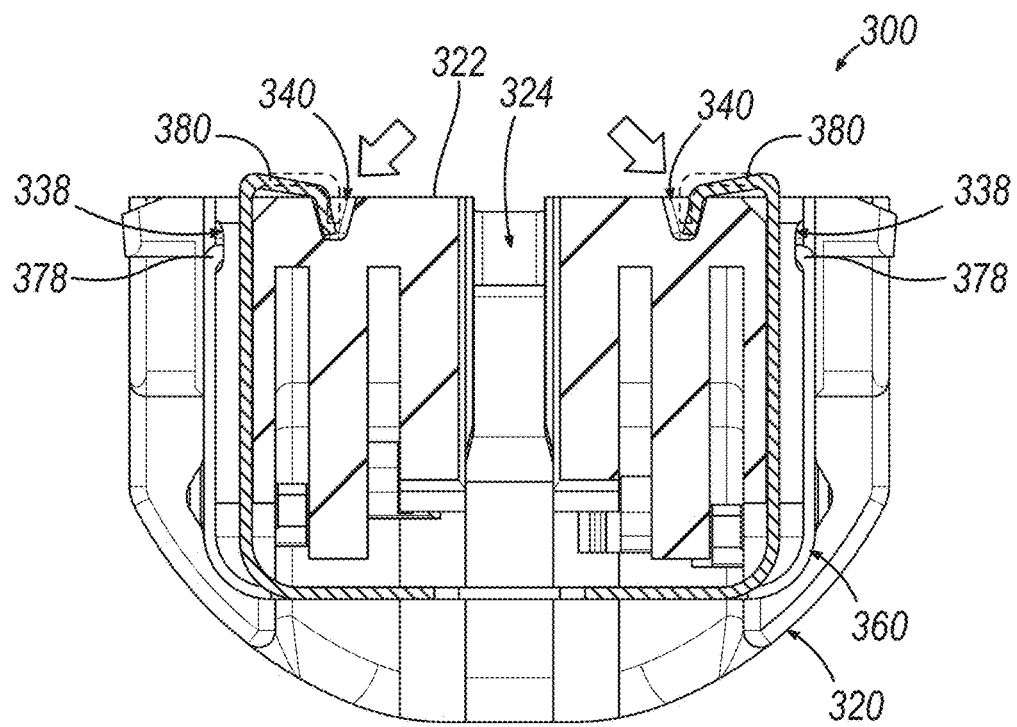
FIG. 12B depicts another rear cross-sectional view of the staple cartridge of FIG. 11, the cross-section taken along line 12-12 of FIG. 11, according to another example of an assembly method.

In other examples, the force described above may be applied in different ways to manipulate proximal tab (380) as discussed above. Although, the different force applications described here are described independently, it should be understood that in some examples different force applications may be applied together to further deform lower cartridge tray (360). FIG. 12B shows another force application for deformation of proximal tab (380). As can be seen, the force application shown in FIG. 12B is substantially similar to the force application shown in FIG. 12A, except the force application in the present example is oriented at about a 45° angle relative to the horizontal extension of proximal tab (380). As with the force application above, the force applied in the present example is generally applied using peening or another pressing means. However, application of the force at a 45° angle may be desirable in some examples to deform either the horizontal extension of proximal tab (380), the vertical extension of proximal tab (380), the 90 bend of proximal tab (380), or some combination thereof.

Figure 13A:
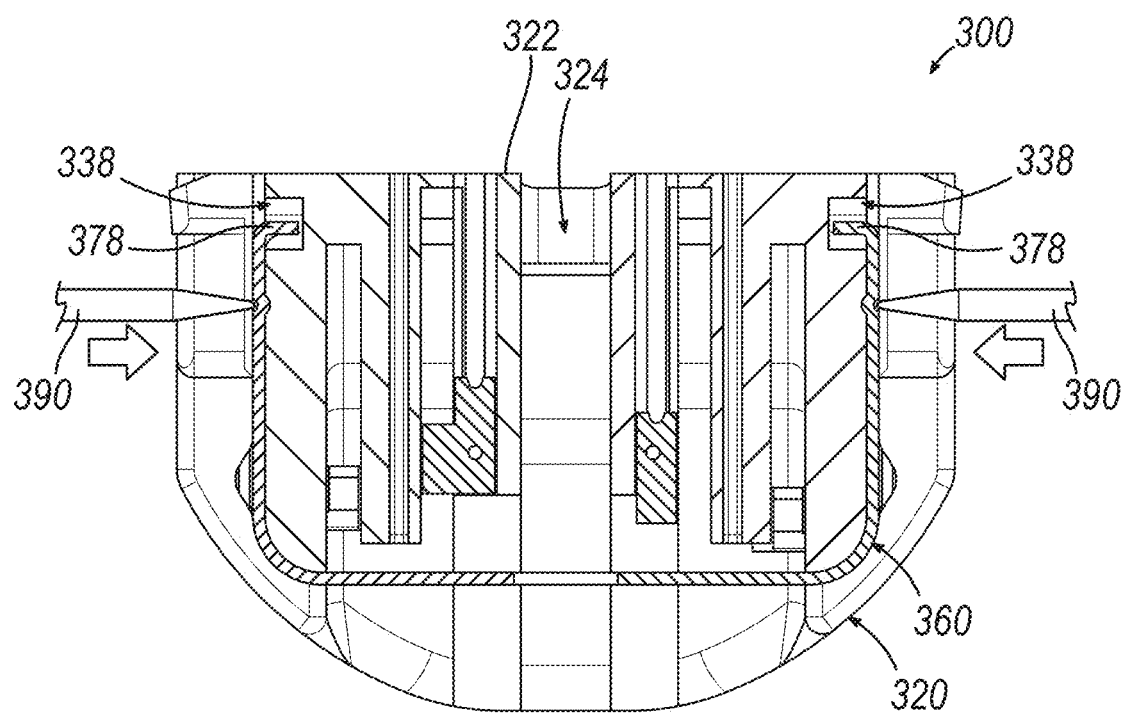
FIG. 13A depicts yet another rear cross-sectional view of the staple cartridge of FIG. 11, the cross-section taken along line 13-13 of FIG. 11, according to another example of an assembly method.

In other examples, it may be desirable to apply the force described above to other portions of lower cartridge tray (360) to deform other portions thereof. For instance, as can be seen in FIG. 13A, in some examples force may be applied to the side of lower cartridge tray (360). In the present example, the force is similarly applied using peening or another pressing means. Such a force may be applied at multiple locations along the length of lower cartridge tray (360) using a pointed peening tool (390). As shown in FIG. 13A, the force results in lower cartridge tray (360) being deformed to have one or more rounded or dome-like indentations similar to a detent feature. This deformation may provide additional fastening between cartridge body (320) and lower cartridge tray (360) by lower cartridge tray (360) digging into the surface of cartridge body (320).

Figure 13B:
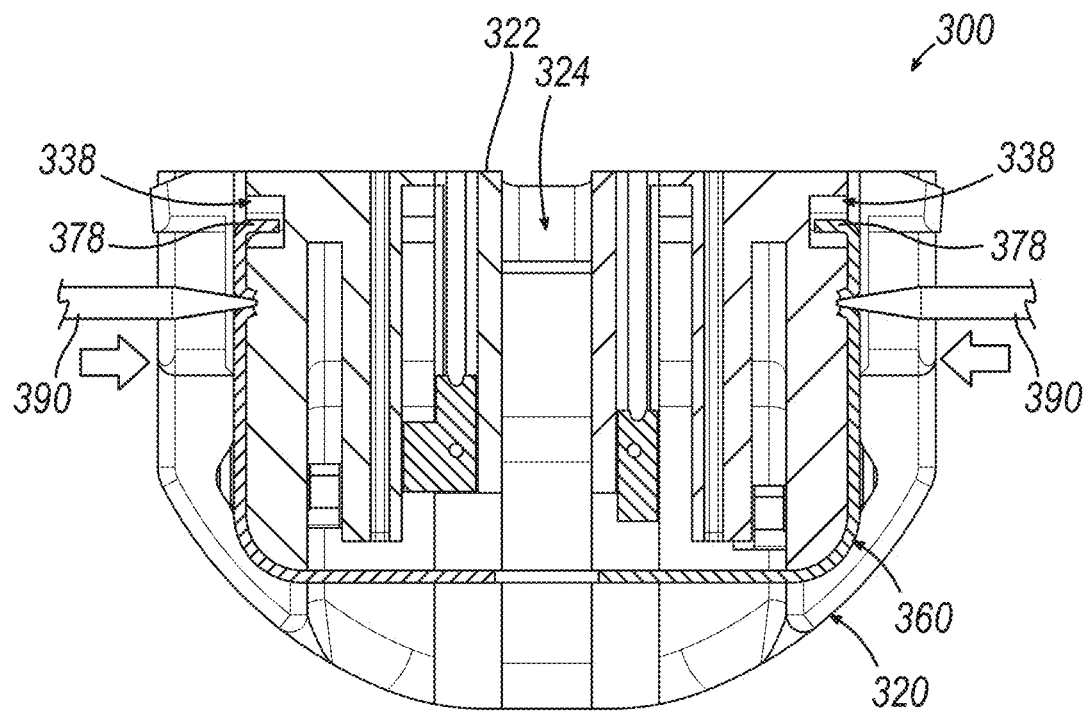
FIG. 13B depicts still another rear cross-sectional view of the staple cartridge of FIG. 11, the cross-section taken along line 13-13 of FIG. 11, according to another example of an assembly method.

In other examples, the force applied may be great enough to pierce lower cartridge tray (360). Such piercing may be desirable to increase engagement between lower cartridge tray (360) and cartridge body (320). For instance, as can be seen in FIG. 13B, piercing tool (390) may be used with sufficient force such that the pointed end thereof penetrates entirely through the side of lower cartridge tray (360) (or any other portion of lower cartridge tray (360)). This penetration may cause portions of lower cartridge tray (360) to extend into the surface of cartridge body (320) to thereby increase coupling between cartridge body (320) and lower cartridge tray (360).

Although not shown, it should be understood that in other examples similar deformation principles may be applied in different ways to increase coupling between cartridge body (320) and lower cartridge tray (360). For instance, in some examples, portions of lower cartridge tray (360) may be slotted to form tabs or engagement sections that may later be deformed by peening and/or other pressing means. By way of example only, in one example, a three-leg rectangle or radial slot may be pre-cut into a portion of lower cartridge tray (360) having a larger cross-sectional area (e.g., the side) to form a tab or other feature. Such a tab may be initially flush with other portions of lower cartridge tray (360). However, once lower cartridge tray (360) is attached to cartridge body (320), such a tab may then be deformed to increase engagement between lower cartridge tray (360) and cartridge body (320). Such a configuration may be desirable in some examples to promote easier or more controlled deformation of lower cartridge tray (360).

IV. EXEMPLARY RETAINER FOR STAPLE CARTRIDGE

In some examples it may be desirable to provide additional coupling mechanism in addition to or in lieu of the coupling features described above with respect to staple cartridges (37, 200, 300). For instance, in some examples it may be desirable to provide an external feature or assembly to physically maintain engagement between structures similar to cartridge bodies (70, 220, 320) and lower cartridge trays (74, 260, 360) described above prior to use of staple cartridge (37, 200, 300) in instrument (10). Such physical engagement structures may then be removed or otherwise disabled upon use of staple cartridge (37, 200, 300) in instrument (10). Such physical engagement structures may be desirable to either simplify the construction of a staple cartridge similar to staple cartridges (37, 200, 300) or to provide an additional coupling mechanism. Examples of such engagement structures are described in greater detail below.

Figure 14:
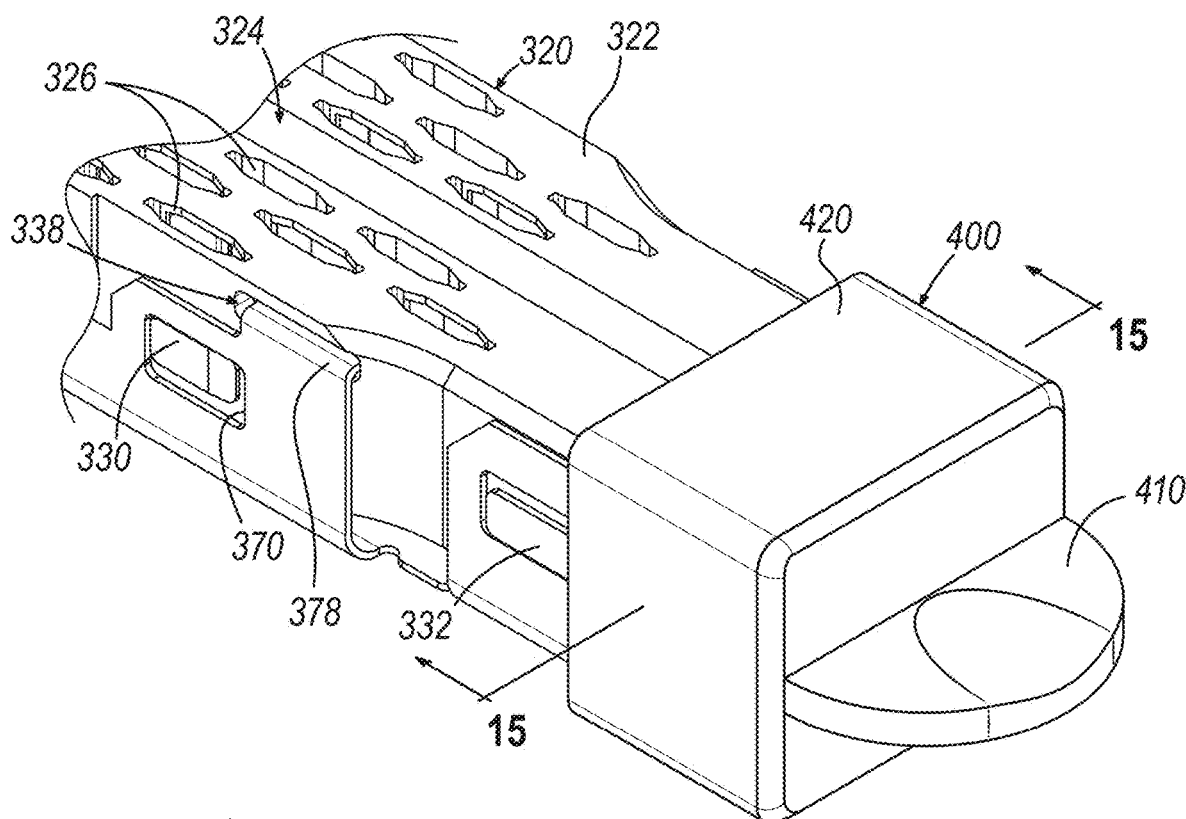
FIG. 14 depicts an enlarged perspective view of the proximal end of the staple cartridge of FIG. 11, the staple cartridge being used with an exemplary retainer.

FIG. 14 shows an exemplary retainer (400) that may be readily used with any one or more of the staple cartridges (37, 200, 300) described herein. Although retainer (400) is shown herein as being used with staple cartridge (300) described above, it should be understood that any other staple cartridge may be used with retainer (400), including staple cartridges (37, 200).

As can be seen, retainer (400) includes a manipulator (410) and a cartridge receiving portion (420). Both manipulator (410) and cartridge receiving portion (420) are generally integrally formed by a plastic material in this example. However, in some examples, it should be understood that various portions of retainer (400) may include metal. For instance, in some examples, cartridge receiving portion (420) may include a metal insert. Such a metal insert may be desirable in some examples to avoid abrasion of cartridge receiving portion (420) by staple cartridge (300). In examples where only plastic is used for retainer (400), certain features of staple cartridge (300) may be modified (e.g., rounded corners and elimination of sharp edges) to also avoid abrasion of receiving portion (420).

Manipulator (410) is generally configured as a tab-like grip for an operator to gasp for manipulation of retainer (400). As will be described in greater detail below, retainer (400) is configured to be detachable from staple cartridge (300). Thus, manipulator (410) may be used for manual detachment. As such, it should be understood that manipulator (410) may take on a variety of forms aside from the rounded tab shown in FIG. 14. For instance, in some examples, manipulator (410) may be an elongate square tab. In addition, or in the alternative, manipulator (410) may include a plurality of grip features, knurling, ribs, and/or etc. Of course, various alternative configurations for manipulator (410) will be apparent to those skilled in the art in view of the teachings herein.

Cartridge receiving portion (420) is generally configured to receive at least a portion of the proximal end of staple cartridge (300). Thus, it should be understood that cartridge receiving portion (420) is generally hollow. In addition, cartridge receiving portion (420) defines a shape closely corresponding to the shape of the proximal end of staple cartridge (300) (e.g., a tight fit). In some versions, cartridge receiving portion (420) includes an elastomeric material that promotes friction between cartridge receiving portion (420) and the proximal end of staple cartridge (300). In addition, or in the alternative, cartridge receiving portion (420) may be slightly undersized relative to the proximal end of staple cartridge (300), to provide an interference fit between cartridge receiving portion (420) and the proximal end of staple cartridge (300). Similarly, the interior of cartridge receiving portion (420) may include bumps, ribs, or other features that provide an interference fit between cartridge receiving portion (420) and the proximal end of staple cartridge (300). In any case, the relationship between cartridge receiving portion (420) and the proximal end of staple cartridge (300) is such that retainer (400) will not inadvertently fall off of the proximal end of staple cartridge (300); yet an operator may intentionally remove retainer (400) from staple cartridge (300) without undue hardship.

Figure 15:
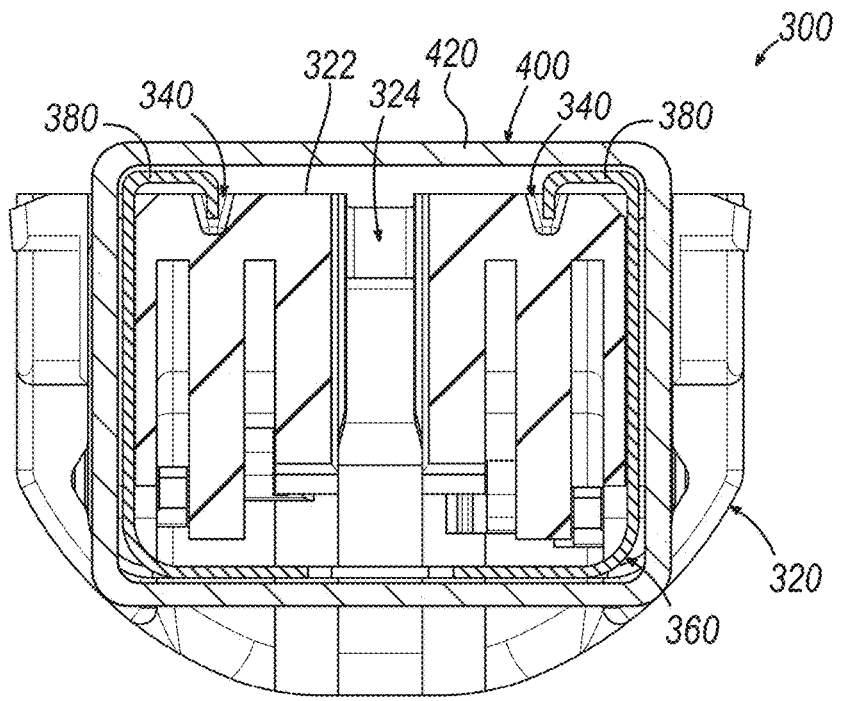
FIG. 15 depicts rear cross-sectional view of the staple cartridge of FIG. 11 with the retainer of FIG. 14 attached thereto, the cross-section taken along line 15-15 of FIG. 14.

As best seen in FIG. 15, cartridge receiving portion (420) closely aligns with the proximal end of staple cartridge (300) to provide minimal clearance between cartridge receiving portion (420) and staple cartridge (300). This minimal clearance is generally desirable to hold cartridge body (320) within lower cartridge tray (360) until staple cartridge (300) is ready for use. Thus, cartridge receiving portion (420) is configured to provide physical containment of the proximal end of staple cartridge (300) until staple cartridge (300) is ready for use.

Figure 16:
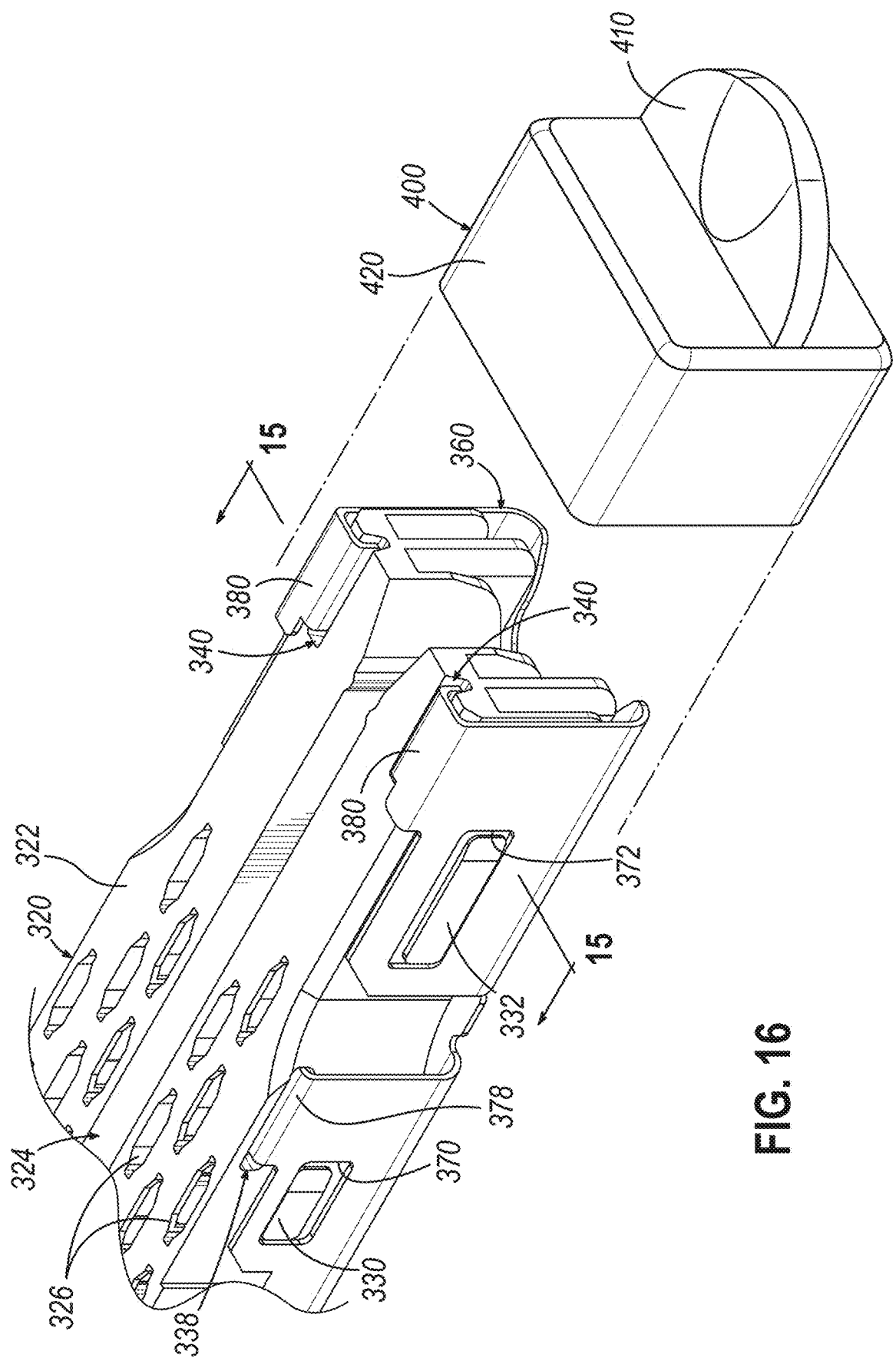
FIG. 16 depicts an exploded perspective view of the proximal end of the staple cartridge of FIG. 11 and the retainer of FIG. 14.

As can be seen in FIG. 16, in use retainer (400) may be selectively attached and subsequently selectively detached from the proximal end of staple cartridge (300). In this use, retainer (400) may be attached after assembly of staple cartridge (300). During attachment, retainer (400) may act as a go/no-go gauge to verify complete coupling between cartridge body (320) and lower cartridge tray (360). Retainer (400) may then remain in place on staple cartridge (300) during transport and storage to maintain alignment between cartridge body (320) and lower cartridge tray (360). Once an operator desires to use staple cartridge (300), retainer (400) may be removed prior to insertion of staple cartridge (300) into instrument (10).

Figure 17:
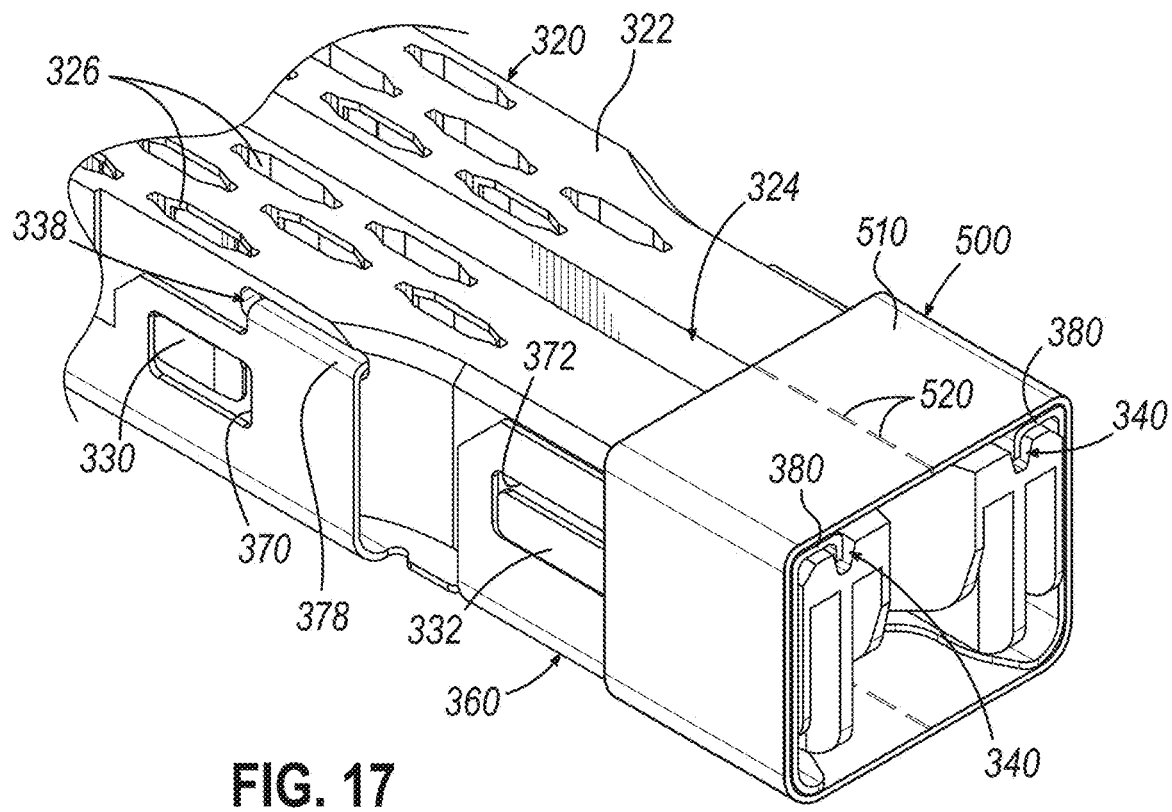
FIG. 17 depicts another enlarged perspective view of the proximal end of the staple cartridge of FIG. 11, the staple cartridge being used with another exemplary retainer.

FIG. 17 shows an exemplary alternative retainer (500) that may be used in lieu of retainer (400) described above. Unless otherwise described herein, retainer (500) of the present example is substantially similar to retainer (400) described above. For instance, retainer (500) is generally configured for use with staple cartridges (37, 200, 300) described herein or any other suitable staple cartridge. Similarly, retainer (500) is also configured to physically engage the proximal end of staple cartridges (37, 200, 300) to maintain alignment between cartridge body (70, 220, 320) and lower cartridge tray (74, 260, 360). In addition, although retainer (500) is described herein as being used with staple cartridge (300), it should be understood that in other examples, retainer (500) may be readily used with any other suitable staple cartridge such as staple cartridges (37, 200) described herein.

Unlike retainer (400) described above, retainer (500) of the present example is generally configured to remain secured to staple cartridge (300). For instance, as can be seen in FIG. 17, retainer (500) includes a hoop portion (510) that extends around the proximal end of staple cartridge (300). Hoop portion (510) of the present example is configured as a thin-film polymer over-wrap. Hoop portion (510) of the present example is further configured to have a tight fit over the proximal end of staple cartridge (300). This tight fit is configured to provide sufficient hoop-stress to maintain alignment between cartridge body (320) may lower cartridge tray (360).

In the present example, the hoop-stress provided by hoop portion (510) is also sufficient to secure retainer (500) to staple cartridge (300). However, it should be understood that in other examples, adhesive backing may be used to provide an adhesive bond between retainer (500) and staple cartridge (300). In such examples, the adhesive backing may be applied to the interior of hoop portion (510).

As noted above, hoop portion (510) comprises a polymer material. In the present example, a bio-implantable/absorbable grade polymer material is used. This bio-implantable/absorbable grade is generally desirable due to the attachment means used for hoop portion (510). For instance, as noted above, hoop portion (510) of the present example only uses hoop-stress to secure retainer (500) to staple cartridge (300). Thus, during a procedure, some or all of retainer (500) could dislodge from staple cartridge (300). Accordingly, it may be desirable for retainer (500) to be bio-implantable/absorbable grade so that it may remain in a patient if needed. By contrast, if hoop portion (510) is secured to staple cartridge (300) by an adhesive backing, hoop portion (510) may comprise a bio-compatible material only, as retainer (500) will remain secured to staple cartridge (300) during use.

Retainer (500) of the present example further includes a plurality of perforations (520) in the surface of hoop portion (510). As can be seen, perforations (520) are generally aligned with vertical slot (324) of staple cartridge (300). This positioning is configured to permit cutting edge (48) of instrument (10) to easily cut through retainer (500) when staple cartridge (300) is used with instrument (10) or otherwise permit easy removal of retainer (500).

In use, retainer (500) may be fastened to the proximal end of staple cartridge (300) during assembly and after coupling between cartridge body (320) and lower cartridge tray (360). Retainer (500) may then hold cartridge body (320) and lower cartridge tray (360) in alignment during transport, storage, or at any other time prior to use with instrument (10). Once an operator desires to use staple cartridge (300), retainer (500) may be detached from staple cartridge (300) by an operator cutting retainer (500) at perforations (520). Alternatively, retainer (500) may remain in place on staple cartridge (300) during use with instrument (10). In this use, retainer (500) may still be cut by cutting edge (48) of instrument (10), yet the severed portions of retainer (500) remain adhered to staple cartridge (300) after retainer (500) is severed by cutting edge (48).

Figure 18:
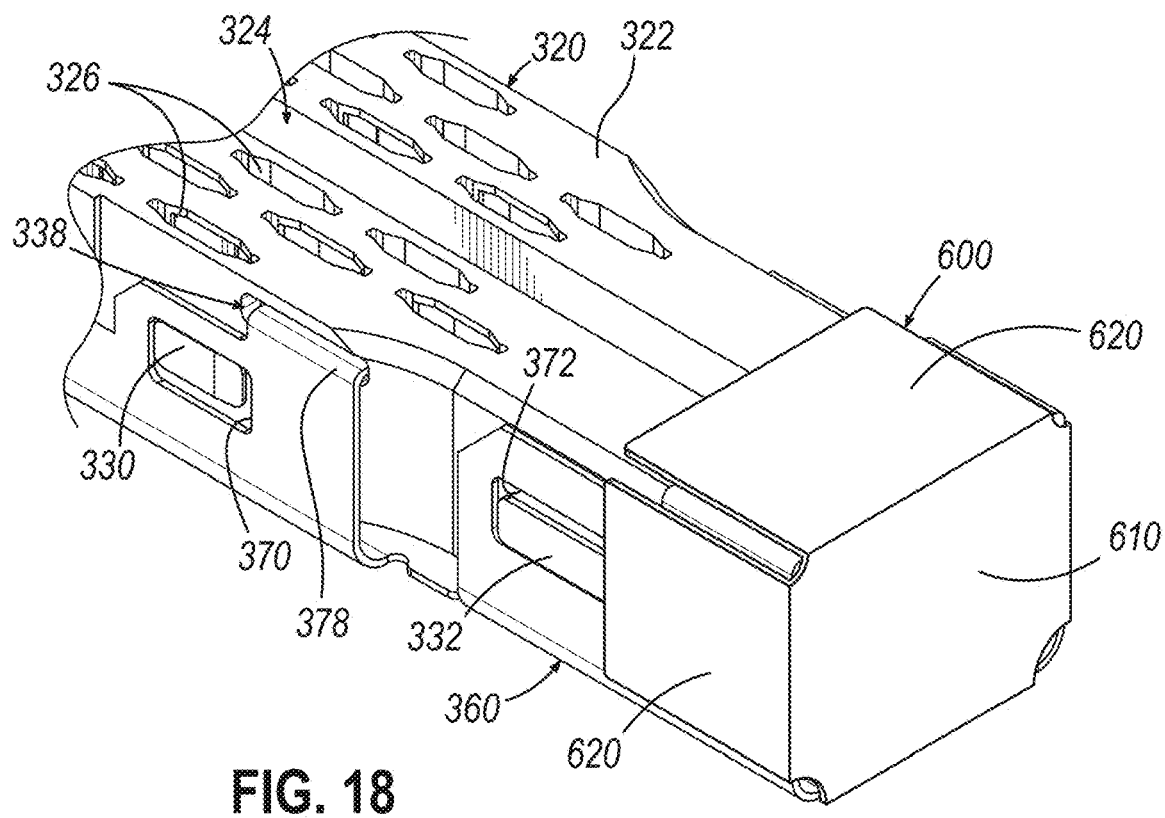
FIG. 18 depicts yet another enlarged perspective view of the proximal end of the staple cartridge of FIG. 11, the staple cartridge being used with yet another exemplary retainer.

FIG. 18 shows another exemplary alternative retainer (600) that may be used in lieu of retainer (400, 500) described above. Unless otherwise described herein, retainer (600) of the present example is substantially similar to retainer (400) described above. For instance, retainer (600) is generally configured for use with staple cartridges (37, 200, 300) described herein or any other suitable staple cartridge. Similarly, retainer (600) is also configured to physically engage the proximal end of staple cartridges (37, 200, 300) to maintain alignment between cartridge body (70, 220, 320) and lower cartridge tray (74, 260, 360). In addition, although retainer (600) is described herein as being used with staple cartridge (300), it should be understood that in other examples, retainer (600) may be readily used with any other suitable staple cartridge such as staple cartridges (37, 200) described herein.

Unlike retainer (400) described above, retainer (600) of the present example is a thin-film laminate including a proximal wall (610) with four tabs (620) extending distally therefrom. Each tab (620) includes an adhesive back such that each tab (620) is configured to stick to a surface of staple cartridge (300). Optionally, proximal wall (610) also includes an adhesive back to stick to one or more proximal surfaces of staple cartridge (300).

As noted above, retainer (600) of the present example comprises a thin film with one or more portions thereof having an adhesive backing. Due to the presence of adhesive, retainer (600) of the present example is configured to remain fixed to staple cartridge (300), even during use of staple cartridge (300). As such, retainer (300) may comprise only a bio-compatible polymer. However, in some examples, bio-implantable/absorbable polymer grades may be used as desired so that portions of retainer (600) may remain within a patient after use of staple cartridge (300).

In use, retainer (600) may initially be planar with all of proximal wall (610) and tabs (620) aligned with a single plane. Retainer (600) may then be applied to staple cartridge (300) by first abutting proximal wall (610) with the proximal end of staple cartridge (300). Each tab (620) may then be bent at approximately 90° relative to proximal wall (610) to adhere to a corresponding surface of staple cartridge (300), thereby attaching retainer (600) to staple cartridge (300). Once retainer (600) is attached to staple cartridge (300), retainer (600) may remain in place during shipping, storage, or any other activity. Once an operator desires to use staple cartridge (300), retainer (600) may be removed by pulling one or more tabs (620) away from a corresponding surface of staple cartridge (300). Alternatively, retainer (600) may remain in place during use of staple cartridge (300) with instrument (10). In such use, it should be understood that cutting edge (48) of instrument (10) may be used to cut through retainer (600) without impacting performance of instrument (10).

Figure 19:
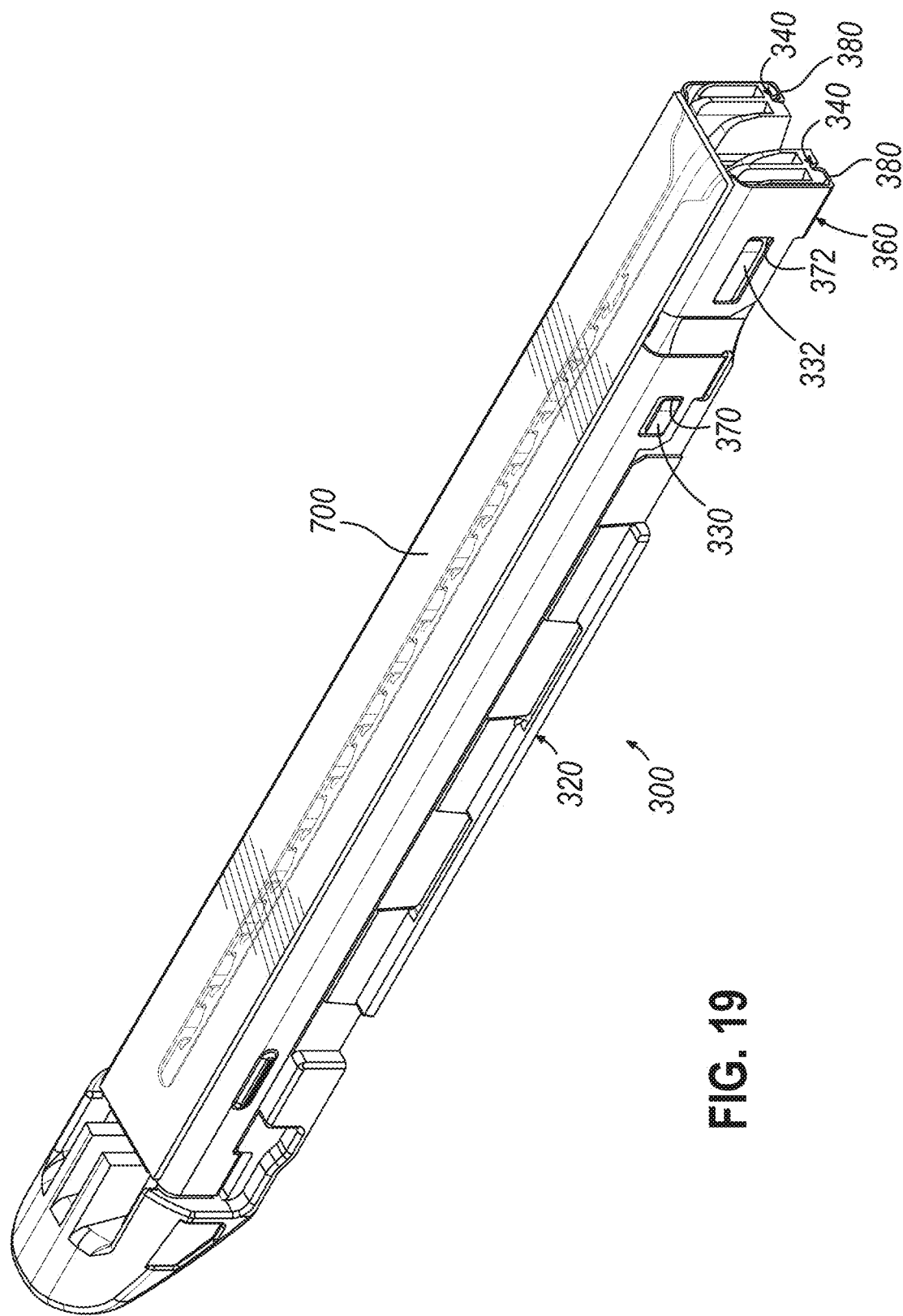
FIG. 19 depicts still another enlarged perspective view of the staple cartridge of FIG. 11, the staple cartridge being used with still another exemplary retainer.

FIG. 19 shows another exemplary alternative retainer (700) that may be used in lieu of, or in addition to, retainer (400, 500, 600) described above. Unless otherwise described herein, retainer (700) of the present example is substantially similar to retainer (400) described above. For instance, retainer (700) is generally configured for use with staple cartridges (37, 200, 300) described herein or any other suitable staple cartridge. Similarly, retainer (700) is also configured to physically engage the proximal end of staple cartridges (37, 200, 300) to maintain alignment between cartridge body (70, 220, 320) and lower cartridge tray (74, 260, 360). In addition, although retainer (700) is described herein as being used with staple cartridge (300), it should be understood that in other examples, retainer (700) may be readily used with any other suitable staple cartridge such as staple cartridges (37, 200) described herein.

Unlike retainer (400) described above, retainer (700) of the present example is a section of bio-compatible tape that is applied to the bottom portion (e.g., opposite of upper deck (322)) of staple cartridge (300). The application of retainer (700) is configured to cover the entire bottom surface of staple cartridge (300), thereby spanning the gap defined by vertical slot (324). This configuration may be desirable to prevent each "leg" of staple cartridge (300) defined by vertical slot (324) from splaying laterally outwardly during shipping, storage, and or handing (or to easily identify when such a condition has occurred due to tearing of retainer (700)). Such splaying is generally an undesirable condition because this may lead to dislodging of components of staple cartridge (300) such as staples, staple drivers, etc.

Although retainer (700) of the present example is shown as covering the entire bottom surface of staple cartridge (300), it should be understood that in other examples this coverage may be varied. For instance, in some examples, retainer (700) may be shortened to only cover a proximal portion of the bottom surface of staple cartridge (300). Still other covering configurations will be apparent to those skilled in the art in view of the teachings herein.

In use, retainer (700) is applied during assembly of staple cartridge (300). In some uses, application may occur either after coupling of cartridge body (320) with lower cartridge tray (360) or prior to coupling. Regardless, once retainer (700) is applied, retainer (700) may remain in place during shipping, handling, and/or storage of staple cartridge (300). Once an operator desires to use staple cartridge (300), retainer (700) may be removed by pulling retainer (700) from staple cartridge (300). Alternatively, retainer (700) may be left in place during use of staple cartridge (300) with instrument (10). During such use, retainer (700) may be easily cut using cutting edge (48) of instrument (10).

V. EXEMPLARY CARTRIDGE WITH HEAT STAKE

Figure 20:
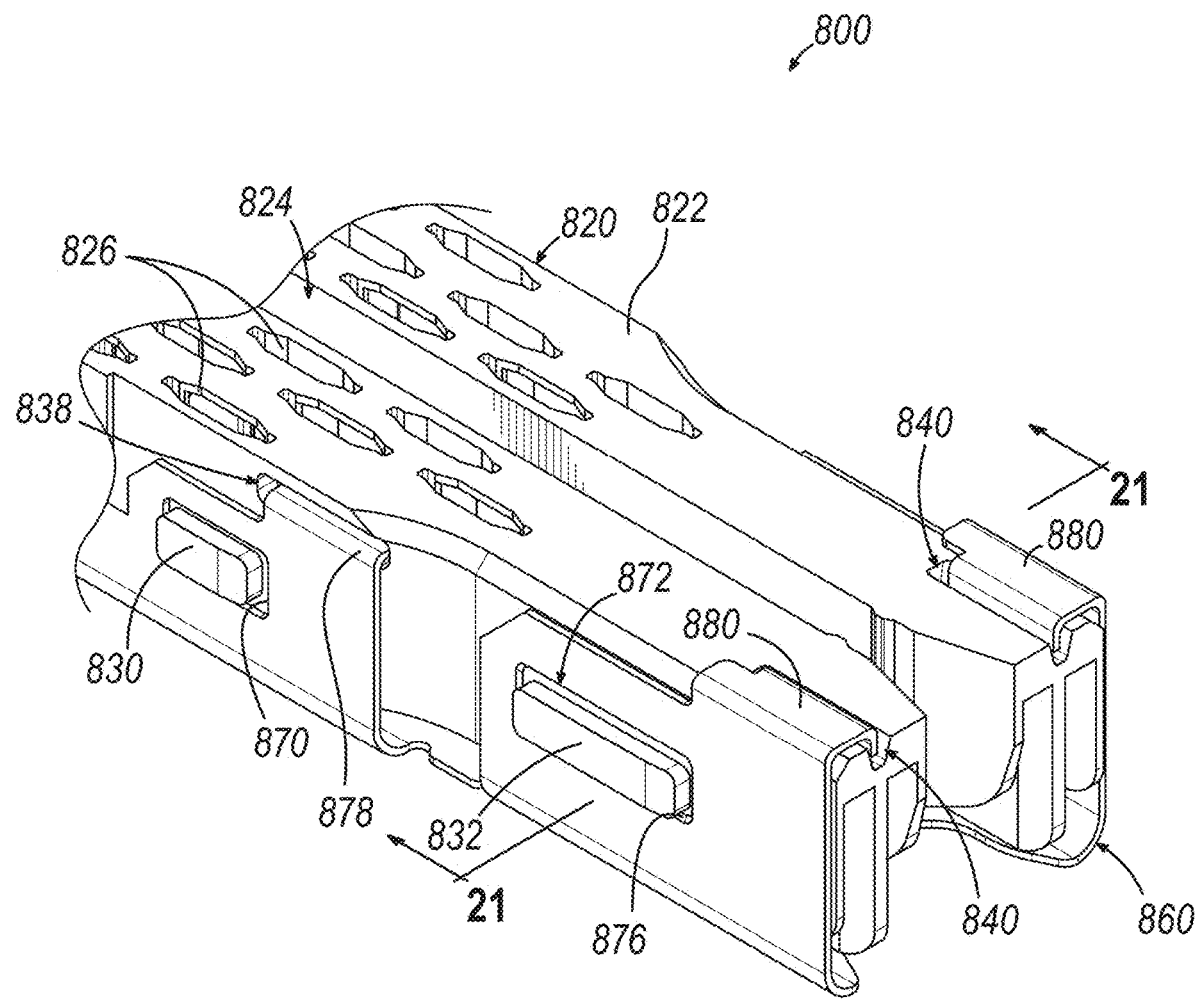
FIG. 20 depicts a perspective view of a proximal end of another exemplary staple cartridge for use with the instrument of FIG. 1.

FIG. 20 shows an exemplary alternative staple cartridge (800) that is configured for use with instrument (10) described above in lieu of staple cartridge (37). Unless otherwise described herein, it should be understood that staple cartridge (800) is substantially similar to staple cartridges (37, 200, 300) described above. For instance, as with staple cartridge (37), staple cartridge (800) of this example includes a cartridge body (820). As similarly discussed above, cartridge body (820) defines an upper deck (822) and is coupled to a lower cartridge tray (860). Upper deck (822) at least partially defines a vertical slot (824) that is formed through part of staple cartridge (800). Upper deck (822) further defines three rows of staple apertures (826) extending through upper deck (822) on one side of vertical slot (824), with another set of three rows of staple apertures (826) being formed through upper deck (822) on the other side of vertical slot (824). Of course, any other suitable number of staple rows (e.g., two rows, four rows, any other number) may be provided.

It should be understood that, like with staple cartridge (37), staple cartridge (800) of the present example is configured for use with wedge sled (41) and firing beam (14) to drive a plurality of staple drivers (not shown). The staple drivers may be captured between cartridge body (820) and tray (860), with wedge sled (41) being located proximal to the staple drivers. Wedge sled (41) is movable longitudinally within staple cartridge (800); while the staple drivers are movable vertically within staple cartridge (800). Staples (not shown) may also be positioned within cartridge body (820), above corresponding staple drivers. Each staple may thus be driven vertically within cartridge body (820) by a corresponding staple driver to drive the staple out through an associated staple aperture (826).

As with staple cartridge (200, 300) described above, staple cartridge (800) of this example includes certain features configured to promote firm retention and alignment between cartridge body (820) and cartridge tray (860). As similarly discussed above, such retention features are generally positioned near the proximal end of staple cartridge (800). This proximal positioning may be generally desirable because movable components of instrument (10) such as firing beam (14) engage directly with the proximal end of staple cartridge (800). Thus, proper alignment between cartridge body (820) and cartridge tray (860) is particularly desirable at the proximal end of staple cartridge (800).

Similar to cartridge body (320) described above, cartridge body (820) likewise includes a side-pocket (838), indentation, or opening on each side of cartridge body (820). Side-pocket (838) is generally configured to receive a corresponding feature of cartridge tray (860) to securely fasten cartridge body (820) to cartridge tray (860). In the present example, side-pocket (838) is configured as a rectangular opening in the side of cartridge body (820). Of course, various other suitable shapes may be used, as will be described in greater detail below. Side-pocket (838) of the present example extends through cartridge body (820) from an exterior surface into an interior cavity of cartridge body (820). Thus, side-pocket (838) of the present example is a through hole. Alternatively, it should be understood that in other examples, side-pocket (838) may extend through only a portion of cartridge body (820) similar to a recess, a groove, or a blind bore.

As with cartridge tray (360) described above, cartridge tray (860) likewise includes a distal tab (878) on each side corresponding to each side-pocket (838) of cartridge body (820). Each distal tab (878) is configured to be received within side-pocket (838) of cartridge body (820) to securely fasten cartridge body (820) to cartridge tray (860). Each distal tab (878) defines an inverted L-shape. Thus, each distal tab (878) includes an approximately 90° bend followed by an inward extension. The particular length of the inward extension for each distal tab (878) may be any suitable amount to promote coupling between cartridge body (820) and cartridge tray (860). For instance, in some examples, the inward extension of each distal tab (878) corresponds to the approximate wall thickness of cartridge body (820). The extension of each distal tab (878) may be configured to hold cartridge body (820) to lower cartridge tray (860) and thus prevent lateral or upward movement of cartridge body (820).

Cartridge body (820) also includes a pair of proximal channels (840) similar to proximal channels (340) described above. As with proximal channels (340), proximal channels (840) are positioned on each side of on the proximal end thereof. Each proximal channel (840) extends downwardly from upper deck (822) into the surface of cartridge body (820) and extends longitudinally along a portion of the length of cartridge body (820). Additionally, each proximal channel (840) is inwardly offset by a predetermined amount from a respective side of cartridge body (820). As will be described in greater detail below, each proximal channel (840) is configured to receive a corresponding retention feature of lower cartridge tray (860).

Lower cartridge tray (860) also includes a proximal tab (880) on each side thereof that is substantially similar to proximal tab (380) described above. As with proximal tab (380), each proximal tab (880) of the present example corresponds to each proximal channel (840) of cartridge body (820). As such, at least a portion of each proximal tab (880) is configured for receipt within a respective proximal channel (840). Each proximal tab (880) includes a double-fold to define a 270° bend. This bend defines a structure similar to a three-sided box. In other words, each proximal tab (880) first extends horizontally and inwardly from the side of lower cartridge tray (860) at about a 90° angle relative to the side of lower cartridge tray (860). Each proximal tab (880) then bends about another 90° and extends downwardly.

As best seen in FIG. 20, cartridge body (820) is similar to cartridge body (320) in that each side of cartridge body (820) includes a distal laterally-extending protrusion (830) and a proximal laterally-extending protrusion (832). Protrusions (830, 832) are generally configured to be received within corresponding windows (870, 872) of cartridge tray (860).

Unlike protrusions (330, 332) described above, protrusions (830, 832) of the present example are generally configured to provide a heat-stake form of engagement with cartridge tray (860). For instance, each protrusion (830, 832) extends outwardly from a side surface of cartridge body (820) and defines generally rectangular shape with rounded corners. The outward extension of each protrusion (830, 832) is generally greater than the thickness of cartridge tray (860). As will be described in greater detail below, this particular outward extension may be desirable to an excess of material for each protrusion (830, 832) that can be subsequently melted to cover at least a portion of cartridge tray (860).

Cartridge tray (860) correspondingly defines a distal window (870) and a proximal window (872) in each side thereof. Unless otherwise described herein, each window (870, 872) is substantially similar to each window (370, 372) described above with respect to staple cartridge (300). For instance, like with each window (370, 372) described above, each window (870, 872) of the present example is configured as a generally rectangular cutout in each side of cartridge tray (860). Thus, each window (870, 872) is configured to receive a corresponding protrusion (830, 832) of cartridge body (820).

Unlike each window (370, 372) described above, one or more of windows (870, 872) of the present example can include a chamfered edge (876) to promote the heat-stake configuration described above. For instance, in the present example proximal window (872) is shown as including a chamfered edge (876). Chamfered edge (876) is generally configured to reduce the thickness of lower cartridge tray (860) in the area adjacent to proximal window (872) to promote the flow of material of cartridge body (820) over lower cartridge tray (860). Although only proximal window (872) is shown as including chamfered edge (876) in the present example, it should be understood that in other examples structures similar to chamfered edge (876) can be added to both windows (870, 872).

Figure 21A:
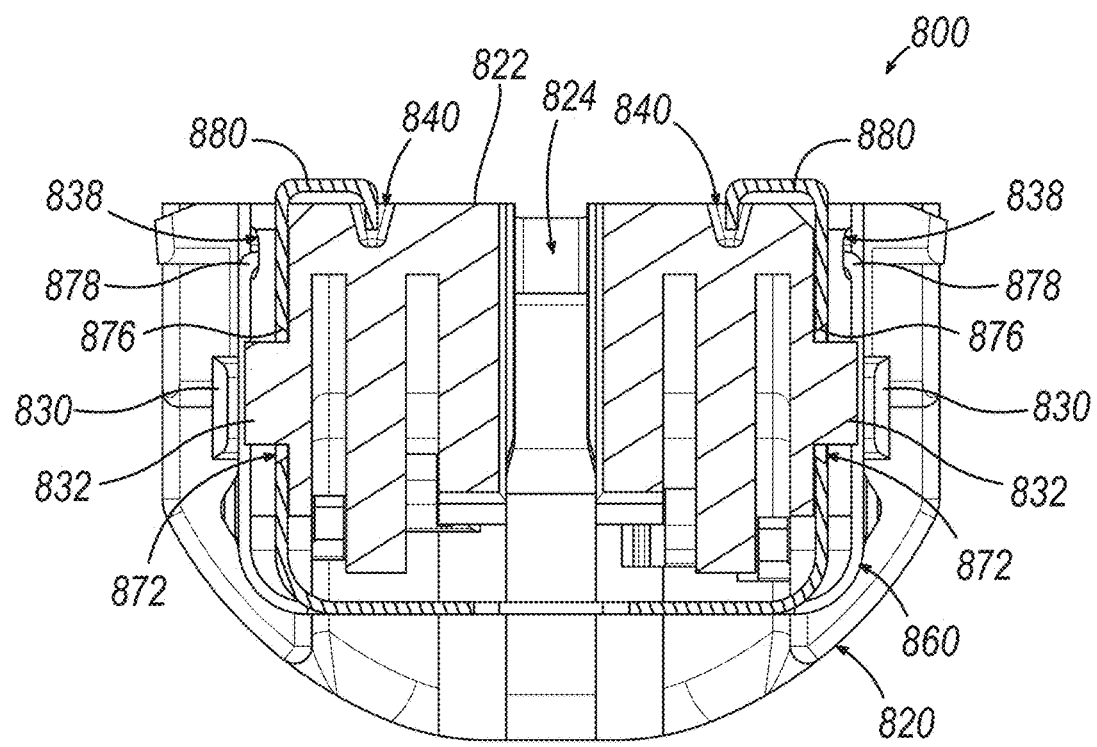
FIG. 21A depicts a rear cross-sectional view of the staple cartridge of FIG. 20, the cross-section taken along line 21-21 of FIG. 20.
Figure 21B:
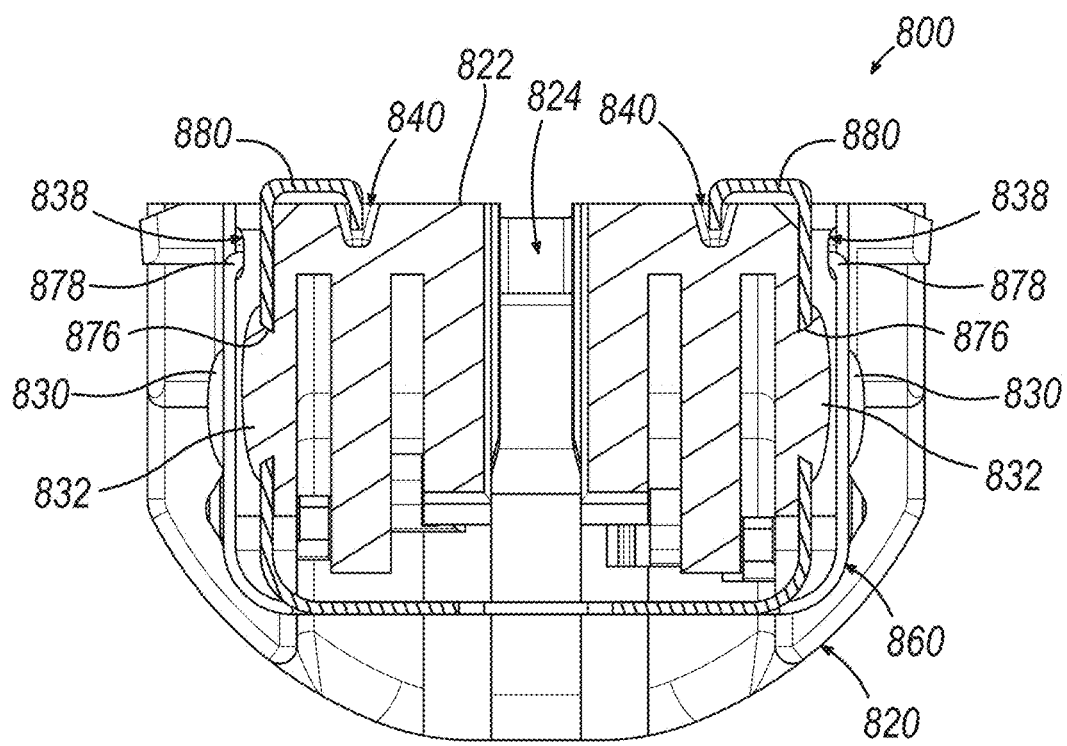
FIG. 21B depicts another rear cross-sectional view of the staple cartridge of FIG. 20, the cross-section taken along line 21-21 of FIG. 20, according to one example of a heat-stake assembly method.

As best seen in FIGS. 21A and 21B, additional fastening in the present example may be provided by heat-staking. Heat-staking involves melting a plastic part using heat such that the plastic part wraps around or covers a portion of an adjacent part. In the present example, this heat-staking is accomplished by applying heat to protrusions (830, 832) of cartridge body (320). As can be seen in FIG. 21A, protrusions (830, 832) initially extend outwardly through windows (870, 872) of lower cartridge tray (860). Heat is then applied to protrusions (830, 832). Heat may be applied in a variety of ways such as by a hot metal surface (e.g., an iron). This heat causes at least some of the excess material of protrusions (830, 832) provided by the additional lateral extension to melt or otherwise deform. Upon melting or otherwise deforming, a portion of each protrusion (830, 832) may mushroom or distort into the configuration shown in FIG. 21B to cover at least a portion of lower cartridge tray (860). Although not shown, it should be understood that in some examples, the process of heat-staking may also include applying a flat tool or other manipulator to each protrusion (830, 832) to thereby manipulate each protrusion (830, 832) into a desired shape. In the present example, one suitable desired shape is flat such that each protrusion (830, 832) is substantially in-plane with lower cartridge tray (860). However, in other examples various alternative shapes can be used.

VI. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument end effector, comprising: (a) a first jaw; (b) a second jaw comprising an anvil having a plurality of staple forming pockets, wherein the first and second jaws are operable to clamp and staple tissue positioned therebetween; (c) a staple cartridge configured for receipt within the first jaw, the staple cartridge including: (i) a cartridge body, (ii) a lower tray, the cartridge body and the lower tray being configured to couple together, and (iii) a plurality of staples; and (d) a retention cap configured to fasten to a proximal end of the cartridge body and to engage the lower tray, the retention cap being further configured to fix the position of the lower tray relative to the cartridge body.

Example 2

The surgical instrument end effector of Example 1, the cartridge body and the retention cap each including one or more complementary ultrasonic welding features.

Example 3

The surgical instrument end effector of Example 1, the complementary ultrasonic welding features including an energy director and an energy well, the energy well being configured to receive the energy director.

Example 4

The surgical instrument end effector of Example 3, the retention cap including the energy director and the cartridge body including the energy well.

Example 5

The surgical instrument end effector of Examples 3 or 4, the energy director including a chamfered portion, the chamfered portion forming an edge configured for engagement with the energy well.

Example 6

The surgical instrument end effector of any one or more of Examples 3 through 5, the energy director being oriented at an oblique angle relative to a longitudinal axis defined by the staple cartridge.

Example 7

The surgical instrument end effector of any one or more of Examples 2 through 5, the complementary ultrasonic welding features including 4 pairs of complementary ultrasonic welding features.

Example 8

The surgical instrument end effector of any one or more of Examples 1 through 7, the lower tray including a tab configured for engagement with the retention cap.

Example 9

The surgical instrument end effector of Example 8, the retention cap including a tab receiver, the tab receiver being configured to receive the tab of the lower tray to trap the tab between the retention cap and the cartridge body.

Example 10

The surgical instrument end effector of any one or more of Examples 8 through 9, the tab of the lower tray including a first leg and a second leg, the first leg extending inwardly from a side of the lower tray, the second leg extending upwardly relative to the first leg.

Example 11

The surgical instrument end effector of Example 10, the tab receiver having a first channel and a second channel, the first channel being configured to receive the first leg of the tab such that the first leg is disposed between an upper surface of the cartridge body and the retention cap.

Example 12

The surgical instrument end effector of Example 11, the second channel being configured to receive the second leg to permit extension of the tab through the retention cap.

Example 13

The surgical instrument end effector of any one or more of the preceding Examples, the cartridge body defining a recess configured for receipt of the retention cap therein.

Example 14

The surgical instrument end effector of any of the preceding Examples, the retention cap having a first side portion and a second side portion, the first side portion and the second side portion being separated by a vertical slot extending through the staple cartridge.

Example 15

A surgical instrument, comprising: (a) a body; (b) a shaft extending distally from the body; and (c) the surgical instrument end effector of claim 1, wherein the surgical instrument end effector is disposed at a distal end of the shaft.

Example 16

A staple cartridge assembly for use with a surgical instrument end effector, comprising: (a) a staple cartridge configured for receipt with a first jaw of the surgical instrument end effector, the staple cartridge including: (i) a cartridge body, (ii) a lower tray coupled with the cartridge body, and (iii) a plurality of staples; and (b) a retainer selectably couplable to one or both of the cartridge body or the lower tray, at a proximal end of the staple cartridge, at least a portion of the retainer being configured to extend around at least a portion of the staple cartridge to secure the position of the cartridge body relative to the lower tray.

Example 17

The staple cartridge assembly of Example 16, the retainer including a grip and a cartridge receiving portion, the cartridge receiving portion being configured to receive the proximal end of the staple cartridge.

Example 18

The staple cartridge assembly of Example 17, the grip being configured for gasping by an operator for removal of the retainer from the staple cartridge prior to the staple cartridge being received in the first jaw of the surgical instrument end effector.

Example 19

A method for securing a lower tray of a staple cartridge to a cartridge body, the method comprising: (a) inserting the cartridge body into the lower tray, the step of inserting including inserting a first tab of the lower tray into a first channel of the cartridge body; (b) applying a force to a first portion of the lower tray or of the cartridge body to deform the first portion and thereby increase engagement between the lower tray and the cartridge body; and (c) further applying the force to the first portion until a predetermined amount of engagement between the lower tray and the cartridge body is achieved.

Example 20

The method of Example 19, the first portion corresponding to a portion of the first tab of the lower tray.

Example 21

The method of any one or more of Examples 19 or 20, the first tab including a first leg and a second leg, the first leg being oriented at about 90° relative to the second leg, the step of applying the force including applying the force at about 90° degree angle relative to the first leg.

Example 22

The method of any one or more of Examples 19 or 20, the first tab including a first leg and a second leg, the first leg being oriented at about 90° relative to the second leg, wherein the step of applying the force includes applying the force at about a 45° degree angle relative to the first leg.

Example 23

The method of any one or more of Examples 19 through 22, the step of applying the force including applying the force using a peening operation.

Example 24

The method of any one or more of Examples 19 through 22, the step of applying the force including applying the force using a pressing operation.

Example 25

The method of any one or more of Examples 19 through 24, the step of applying the force including applying the force to both a side of the lower tray and the and the first tab.

Example 26

The method of any one or more of Examples 19 through 25, the step of applying the force being performed using a tool having a sharp tip, the step of applying the force including penetrating at least a portion of the lower tray to deform at least some of the lower tray into a surface of the cartridge body.

Example 27

The method of Example 19, the cartridge body including a first protrusion, the lower tray including a first window configured to receive the first protrusion of the cartridge body, the first portion corresponding to the first protrusion of the cartridge body.

Example 28

The method of Example 27, the first window including a chamfered edge.

Example 29

The method of any one or more of Examples 19 through 27, wherein the step of applying force includes applying at least some heat to the cartridge body.

Example 30

The method of any one or more of Examples 19 through 27, wherein the step of applying force includes using a heat-staking process.

Example 31

A staple cartridge assembly for use with a surgical instrument end effector, comprising: (a) a staple cartridge configured for receipt within a first jaw of the surgical instrument end effector, the staple cartridge including: (i) a cartridge body, (ii) a lower tray, the cartridge body and the lower tray being configured to couple together, and (iii) a plurality of staples; (b) a retention cap configured to fasten to a proximal end of the cartridge body and to engage the lower tray, the retention cap being further configured to fix the position of the lower tray relative to the cartridge body; and (c) a retainer selectably couplable to a proximal end of the staple cartridge, at least a portion of the retainer configured to extend around the staple cartridge to secure the position of the cartridge body relative to the lower tray.

Example 32

A staple cartridge assembly for use with a surgical instrument end effector, comprising: (a) a staple cartridge configured for receipt within a first jaw of the surgical instrument end effector, the staple cartridge including: (i) a cartridge body, (ii) a lower tray, the cartridge body and the lower tray being configured to couple together, and (iii) a plurality of staples; and (b) a retention cap configured to fasten to a proximal end of the cartridge body and to engage the lower tray, the retention cap being further configured to fix the position of the lower tray relative to the cartridge body.

Example 33

A method for use with the staple cartridge assembly of Example 32, the method comprising: applying a force to the lower tray to deform a portion thereof into increased engagement with the cartridge body.

VI. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they may be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that may penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument end effector, comprising:
   (a) a first jaw;
   (b) a second jaw comprising an anvil having a plurality of staple forming pockets, wherein the first and second jaws are operable to clamp and staple tissue positioned therebetween;
   (c) a staple cartridge configured for receipt within the first jaw, the staple cartridge including:
      (i) a cartridge body extending distally from a proximal end to a distal end,
      (ii) a lower tray, the cartridge body and the lower tray being configured to couple together, and
      (iii) a plurality of staples; and
   (d) a retention member configured to fasten to the proximal end of the cartridge body and to engage the lower tray, the retention member being further configured to fix the position of the lower tray relative to the cartridge body, wherein a distal end of the retention member is proximally positioned relative to the plurality of staples.

2. The surgical instrument end effector of claim 1, the cartridge body and the retention member each including one or more complementary ultrasonic welding features.

3. The surgical instrument end effector of claim 2, the complementary ultrasonic welding features including an energy director and an energy well, the energy well being configured to receive the energy director.

4. The surgical instrument end effector of claim 3, the retention member including the energy director and the cartridge body including the energy well.

5. The surgical instrument end effector of claim 3, the energy director including a chamfered portion, the chamfered portion forming an edge configured for engagement with the energy well.

6. The surgical instrument end effector of claim 3, the energy director being oriented at an oblique angle relative to a longitudinal axis defined by the staple cartridge.

7. The surgical instrument end effector of claim 2, the complementary ultrasonic welding features including 4 pairs of complementary ultrasonic welding features.

8. The surgical instrument end effector of claim 1, the lower tray including a tab configured for engagement with the retention member.

9. The surgical instrument end effector of claim 8, the retention member including a tab receiver, the tab receiver being configured to receive the tab of the lower tray to trap the tab between the retention member and the cartridge body.

10. The surgical instrument end effector of claim 9, the tab of the lower tray including a first leg and a second leg, the first leg extending inwardly from a side of the lower tray, the second leg extending upwardly relative to the first leg.

11. The surgical instrument end effector of claim 10, the tab receiver having a first channel and a second channel, the first channel being configured to receive the first leg of the tab such that the first leg is disposed between an upper surface of the cartridge body and the retention member.

12. The surgical instrument end effector of claim 11, the second channel being configured to receive the second leg to permit extension of the tab through the retention member.

13. The surgical instrument end effector of claim 1, the cartridge body defining a recess configured for receipt of the retention member therein.

14. The surgical instrument end effector of claim 1, the retention member having a first side portion and a second side portion, the first side portion and the second side portion being separated by a vertical slot extending through the staple cartridge.

15. A surgical instrument, comprising:
(a) a body;
(b) a shaft extending distally from the body; and
(c) the surgical instrument end effector of claim 1, wherein the surgical instrument end effector is disposed at a distal end of the shaft.

16. The surgical instrument end effector of claim 1, wherein the retention member includes a retention cap.

17. A staple cartridge assembly for use with a surgical instrument end effector, comprising:
(a) a staple cartridge configured for receipt within a first jaw of the surgical instrument end effector, the staple cartridge including:
(i) a cartridge body extending distally along a longitudinal axis,
(ii) a lower tray coupled with the cartridge body, and
(iii) a plurality of staples; and
(b) a retainer selectably couplable to one or both of the cartridge body or the lower tray at a proximal end of the staple cartridge, at least a portion of the retainer being configured to extend completely around the longitudinal axis and the staple cartridge to secure the position of the cartridge body relative to the lower tray.

18. The staple cartridge assembly of claim 17, the retainer including a grip and a cartridge receiving portion, the cartridge receiving portion being configured to receive the proximal end of the staple cartridge.

19. A staple cartridge assembly for use with a surgical instrument end effector, comprising:
(a) a staple cartridge configured for receipt within a first jaw of the surgical instrument end effector, the staple cartridge including:
(i) a cartridge body extending distally along a longitudinal axis,
(ii) a lower tray coupled with the cartridge body, and
(iii) a plurality of staples; and
(b) a retainer selectably couplable to one or both of the cartridge body or the lower tray at a proximal end of the staple cartridge, at least a portion of the retainer being configured to extend around the longitudinal axis and at least a portion of the staple cartridge to secure the position of the cartridge body relative to the lower tray, wherein the retainer includes a proximal wall configured to enclose proximal ends of the cartridge body and the lower tray.

20. The staple cartridge assembly of claim 19, wherein the proximal wall includes a user grasping feature configured to be grasped by a user.

* * * * *